US009724434B2

(12) United States Patent
Oohashi et al.

(10) Patent No.: US 9,724,434 B2
(45) Date of Patent: Aug. 8, 2017

(54) LYSINE OLIGOMER DERIVATIVE AND CARTILAGE TISSUE MARKER MADE THEREOF

(71) Applicant: NATIONAL UNIVERSITY CORPORATION OKAYAMA UNIVERSITY, Okayama-shi (JP)

(72) Inventors: Toshitaka Oohashi, Okayama (JP); Hiroki Kakuta, Okayama (JP)

(73) Assignee: NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 0 days.

(21) Appl. No.: 14/383,976

(22) PCT Filed: Mar. 13, 2013

(86) PCT No.: PCT/JP2013/056974
§ 371 (c)(1),
(2) Date: Sep. 9, 2014

(87) PCT Pub. No.: WO2013/137302
PCT Pub. Date: Sep. 19, 2013

(65) Prior Publication Data
US 2015/0080551 A1     Mar. 19, 2015

(30) Foreign Application Priority Data

Mar. 13, 2012  (JP) ................................ 2012-055511

(51) Int. Cl.
| A61K 49/00 | (2006.01) |
| C07K 7/02 | (2006.01) |
| A61K 49/04 | (2006.01) |
| C07K 5/02 | (2006.01) |
| A61K 47/48 | (2006.01) |
| A61K 49/08 | (2006.01) |
| A61K 51/04 | (2006.01) |

(52) U.S. Cl.
CPC .... *A61K 49/0056* (2013.01); *A61K 47/48315* (2013.01); *A61K 49/0021* (2013.01); *A61K 49/0442* (2013.01); *A61K 49/085* (2013.01); *A61K 51/0497* (2013.01); *C07K 5/0215* (2013.01); *C07K 7/02* (2013.01)

(58) Field of Classification Search
CPC .......... A61K 49/0056; A61K 47/48315; A61K 49/0021; A61K 49/0442; A61K 49/085; A61K 51/0497; C07K 5/0215; C07K 7/02
See application file for complete search history.

(56) References Cited

U.S. PATENT DOCUMENTS

| 5,756,066 A * | 5/1998 | Nitecki ................ C07K 14/001 424/1.65 |
| 2011/0158909 A1 * | 6/2011 | Grinstaff et al. ............. 424/9.1 |
| 2012/0122788 A1 * | 5/2012 | Kuebelbeck et al. ....... 514/15.4 |

FOREIGN PATENT DOCUMENTS

| EP | 1 120 428 | 8/2001 |
| JP | 10-502807 A | 3/1998 |
| JP | 2003-225093 A | 8/2003 |
| JP | 2003-335857 A | 11/2003 |
| JP | 2004-024855 A | 1/2004 |
| JP | 2005-055224 A | 3/2005 |
| JP | 4089292 B * | 5/2008 | ............. C08G 69/48 |
| JP | 2009-023993 A | 2/2009 |
| JP | 2009023993 * | 2/2009 | ............. A61K 49/00 |
| WO | WO 96/01847 A1 | 1/1996 |
| WO | WO 2005/068645 | 7/2005 |
| WO | WO 2008/078190 | 7/2008 |
| WO | WO 2012/143508 | 10/2012 |

OTHER PUBLICATIONS

Biomedical Applications of Chemically and Microbiologically Synthesized Poly(Glutamic Acid) and Poly(Lysine), Mini-Reviews in Med. Chem., 2004, 4, 179-188, Shi et al.*
Hiraki et al., Use of ADME studies to confirm the safety of e-polylysine as a preservative in food, Regulatory Toxicology and Pharmacology 37 (2003) 328-34.*
Excerpt providing definition from The American Heritage Science Dictionary, 2002, Houghton Mifflin, definition for oligomer. 1 page.*
Gromme et al., The rational design of Tap inhibitors using peptide substrate modifications and peptidomimetics, European Journal of Immunology (1997), 27(4), 898-904.*
Rudat et al., Photophysical properties of fluorescently-labeled peptoids, Eur. Ji. Med. Chem. 46 (2011) 4457-4465.*
Uchiyama et al., Fluorescence characteristics of six 4,7-disubstituted benzofurazan compounds: an experimental and semi-empirical MO study, J. Chem. Soc., Perkin Trans. 2, 1999, 2525-2532.*
Liu and Julian, Deciphering the Peptide Iodination Code: Influence on Subsequent Gas-Phase Radical Generation with Photodissociation ESI-MS, J Am Soc Mass Spectrom 2009, 20, 965-971.*
Poveda et al., Intrinsic Tyrosine Fluorescence as a Tool to Study the Interaction of the Shaker B "Ball" Peptide with Anionic Membranes, Biochem. 2003, 42, 7124-7132.*
International Search Report (PCT/ISA/210) mailed on May 28, 2013, by the Japanese Patent Office as the International Searching Authority for International Application No. PCT/JP2013/056974.

(Continued)

*Primary Examiner* — Lianko Garyu
*Assistant Examiner* — Joseph Fischer
(74) *Attorney, Agent, or Firm* — Buchanan, Ingersoll & Rooney PC

(57) ABSTRACT

There is provided a lysine oligomer derivative, wherein an ε-amino group and a carboxyl group of lysines are linked via a peptide bond, and a group capable of generating or absorbing electromagnetic wave is bonded to a C-terminal carboxyl group, an N-terminal amino group and/or an α-amino group. This lysine oligomer derivative has the characteristic of specifically accumulating in the cartilage matrix and can generate or absorb an electromagnetic wave, and is, therefore, useful as a cartilage tissue marker.

6 Claims, 2 Drawing Sheets

(56) References Cited

OTHER PUBLICATIONS

Manabu Yoshitani et al., "Kansetsu Nankotsu ni Tokuiteki ni Ketsugo suru X Sen Zoeika Imaging Probe no Soshutsu Kenkyu", The Phamaceutical Society of Japan Dai 132 Nenkai Yoshishu 2, Mar. 5, 2012, p. 271, 30P2-pm134.
K. Inagawa et al., "Optical Imaging of Mouse Articular Cartilage Using the Glycosaminoglycans Binding Property of Fluorescent-Labeled Octaarginine", Osteoarthritis and Cartilage, (2009), 17, pp. 1209-1218, 2009 Osteoarthritis Research Society International, Published by Elsevier Ltd.
Fu et al., *Dendritic Iodinated Contrast Agents with PEG-Cores for CT Imaging: Synthesis and Preliminary Characterization*, 17 Bioconjugate Chem. 1043-1056 (2006).
Grandjean et al., *Convergent Synthesis of Fluorescein-labelled Lysine-based Cluster Glycosides*, 40 Tetrahedron Letters 7235-7238 (1999).
Trubetskoy et al., *Block-copolymer of Polyethylene Glycol and Polylysine as a Carrier of Organic Iodine: Design of Long-circulating Particulate Contrast Medium for X-ray Computed Tomography*, 4(6) Journal of Drug Targeting 381-388 (1997).
European Search Report dated Oct. 30, 2015, issued in corresponding EP Application No. 13761422.8-1453.

\* cited by examiner

[FIG. 1]
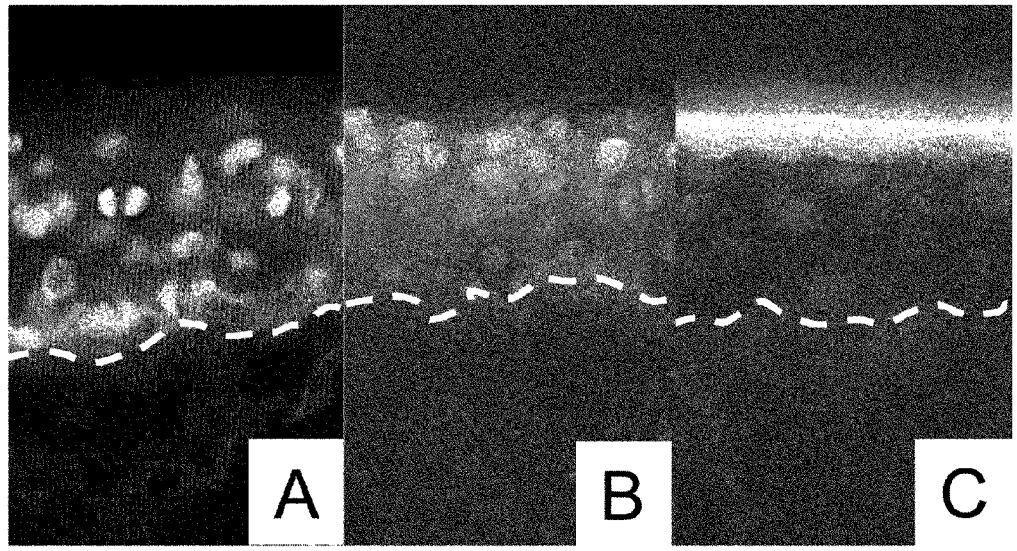
[FIG. 2]
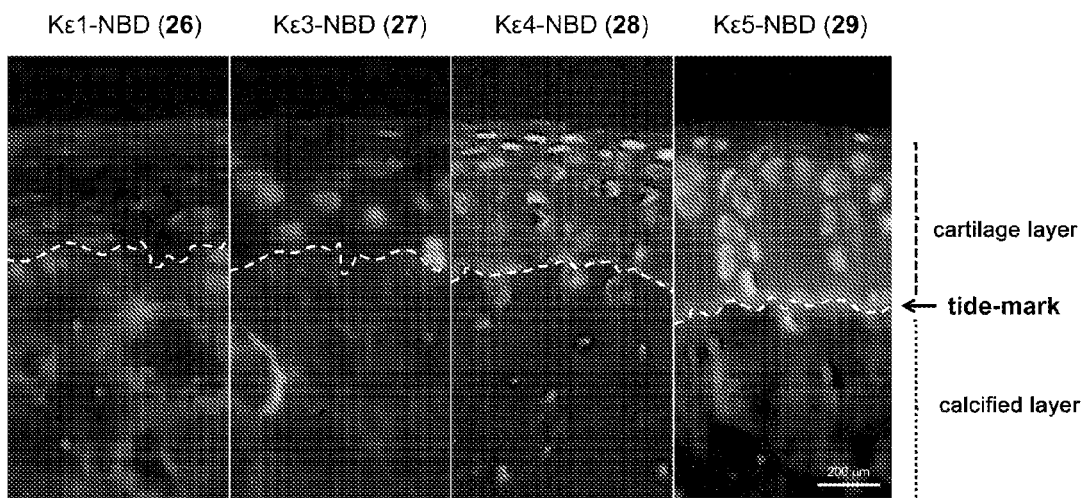

[FIG. 3]
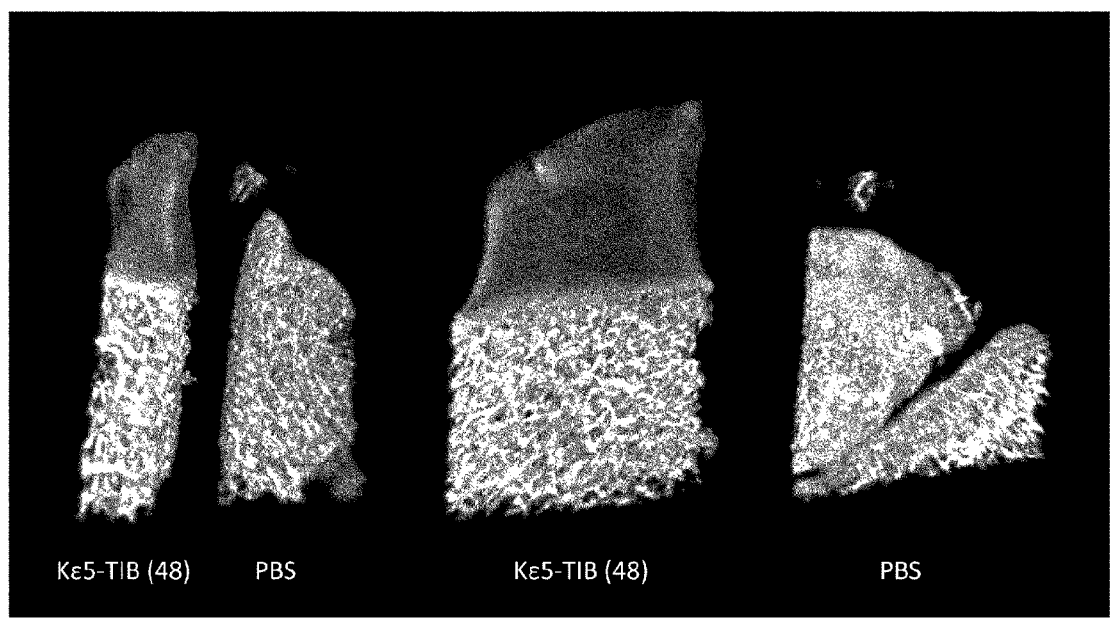

LYSINE OLIGOMER DERIVATIVE AND CARTILAGE TISSUE MARKER MADE THEREOF

TECHNICAL FIELD

The present invention relates to a lysine oligomer derivative. The present invention also relates to a cartilage tissue marker made of a lysine oligomer derivative which specifically binds to a cartilage matrix.

BACKGROUND ART

A cartilage tissue is a supporting tissue consisting cartilage cells and an extracellular matrix surrounding them, which is present for alleviating friction generated between bones and absorbing impact in a joint such as a knee joint. When a cartilage matrix forming the cartilage tissue is degenerated due to a variety of causes, water content is so reduced that its function cannot be maintained, leading to onset of osteoarthritis (OA), which is an arthritic disorder associated with chronic arthritis. It is a disease which degenerates joint components, leading to destruction of a cartilage as well as proliferative change of a bone and a cartilage. The total number of patients with osteoarthritis in Japan is estimated to be about eight millions, and the patients are expected to further increase as the population ages.

Once osteoarthritis develops damage and destruction of a cartilage and a bone, they cannot be restored to their original state later. However, early detection and proper treatment can delay the progression of symptoms. Appearance and development of symptoms of osteoarthritis differ greatly in individuals. For selecting proper treatment, it is, therefore, crucially important that each patient is early and thoroughly examined for the condition of an articular cartilage to find abnormalities. Likewise, aside from clinical practice, it is also crucially important for developing a highly effective therapeutic agent for degeneration of an articular tissue, at least degeneration of an articular cartilage of an experimental animal can be evaluated qualitatively and quantitatively, and furthermore, wherever possible, in the living state (in vivo) over time.

Currently, articular examination in a human patient is conducted generally by plain X-ray photography, arthrocentesis, arthroscopy or the like. Plain X-ray examination is inexpensive and practicable for any medical institution, but an articular cartilage cannot be imaged by X-ray examination because main components of an articular cartilage are aggrecan as a proteoglycan containing chondroitin sulfate and keratan sulfate side chains and collagen. It can be applied to an experimental animal. Therefore, X-ray photography can determine the degree of articular destruction by checking bone change around the joint such as narrowing of a cleft between articulations (cleft between two bone ends which mutually face in a joint), but can only conduct indirect evaluation for change in the cartilage itself. In other words, X-ray photography cannot directly detect the degree of actual destruction or degeneration of the cartilage, and therefore, cannot quantify the degree or find destruction of the articular cartilage in the mildly symptomatic state. Arthrocentesis as an alternative method can determine the state of an articular cartilage by the use of physiological or biochemical changes as indicators, but is ineffective for determining physical conditions such as a thickness and deformation of an articular cartilage. Furthermore, an articular cartilage can be directly imaged for diagnosis by arthroscopic methods. These include a method for determining physical properties of a cartilage by irradiating a cartilage tissue with a laser from the tip of an arthroscope and then detecting ultrasound generated from the tissue (see Patent Reference No. 1) and a method for objectively evaluating the degree of degeneration of a cartilage from an early stage by determining variation over time in an absorbance associated with compressional deformation of the cartilage by the use of a near-infrared aquameter (see Patent Reference No. 2). Any of these methods, however, highly invasive and thus has a problem of imposing a heavy physical burden and infection risk on a patient. These methods can be, therefore, applied to limited cases for a human patient, and even for an experimental animal, these methods are less applicable because such invasion makes it difficult to perform serial examination required for drug evaluation for an arthritic disorder.

On the other hand, MRI has been increasingly employed cartilage imaging in a human patient and is expected to be as an examining means which allows for qualitative evaluation of a cartilage itself. An MRI machine is, however, so expensive that a limited number of medical institutions can introduce an MRI machine. Furthermore, its unsatisfactory resolution also makes it difficult to use the device for the above purpose.

In these circumstances, attempts have been made for developing a method for early diagnosis of the condition of a cartilage and an accurate disease marker therefor (Patent Reference Nos. 3 and 4).

Meanwhile, a fluorometric imaging device for conducting optical projection tomography (OPT) of a body tissue ex vivo using a fluorescent molecule has been developed as technique for selectively constructing a three-dimensional image of a tissue inside the body. According to this technique, a fluorescently-stained living tissue is irradiated with pulse laser as excitation light, and for each pulse irradiation, photons generated from the irradiated site in the living tissue are amplified by a photomultiplier and then detected. The detected signal is processed by a time-correlated single-photon counting method, and the resulting data can be imaged to provide any sectional image of the target tissue or an image of the whole tissue (three-dimensional image, sectional image). Furthermore, an in vivo fluorometric imaging system has been recently developed and commercially available, which can detect the location of a fluorescently-labeled substance in the body of an small animal such as a living rat or mouse from the outside for imaging (for example, GE HEALTHCARE, "eXplore Optix"). According to the system, a fluorescent label which specifically accumulates in a target tissue is administered and its three-dimensional distribution can be determined over time to be imaged. In vivo fluorometric imaging, which is noninvasive and thus safe and has high sensitivity has been increasingly employed to image a marked particular tissue or its component in a living experimental animal over time for evaluating the kinetics of a protein or change in the status of a lesion, and is expected to be similarly utilized for a human tissue in the future.

There has been recently reported a cartilage marker utilizing the property that a polyarginine peptide (a) or polylysine peptide (b) having the structure shown below is specifically bonded to a cartilage tissue (see Patent Reference No. 5). These polypeptides have a structure that an α-amino group and a carboxyl group in arginines or lysines are bonded via a peptide bond, as shown in the following formulas. A compound described in Patent Reference No. 5 is a cartilage tissue marker in which a fluorescent group or an X-ray absorbing group is bonded to an N-terminus or C-terminus.

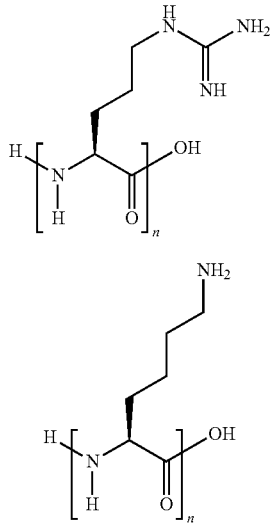

a b

For the compound described in Patent Reference No. 5, in the case of introducing a fluorescent substance, a high-sensitive fluorescent group can be introduced to visualize a desired cartilage tissue. Meanwhile, when an X-ray absorbing substance is used, it must contain many X-ray absorbing atomic group such as iodine atoms. However, a polyarginine peptide or polylysine peptide has a large molecular weight, so that the number of iodine atoms to be introduced in one oligomer molecule must be large. It can affect solubility of the polyarginine peptide or the polylysine peptide or permeability of the compound in a cartilage tissue. Thus, there is room for improvement.

Patent Reference No. 6 has described an E-polylysine in which an amino group is protected by an urethane bond. Herein, an ε-polylysine has a structure that an ε-amino group and a carboxyl group of lysines are linked via a peptide bond. Patent Reference No. 6 has described that such an ε-polylysine is used for bathroom furnishings, cosmetics, feed additives, medical drugs, pesticides, food additives, electronic materials or the like. There are, however, no descriptions about the use of such an ε-polylysine as a marker for a living tissue or about introduction of a fluorescent group or a group for radiographic visualization to an ε-polylysine.

PRIOR ART REFERENCES

Patent References

Patent Reference No. 1: JP 2004-024855 A
Patent Reference No. 2: JP 2005-055224 A
Patent Reference No. 3: JP 2003-225093 A
Patent Reference No. 4: JP 10-502807 A
Patent Reference No. 5: JP 2009-023993 A
Patent Reference No. 6: JP 2003-335857 A

PROBLEM TO BE SOLVED BY THE INVENTION

An objective of the present invention is to provide a lysine oligomer derivative which is specifically bonded to a cartilage tissue. Another objective is to provide a cartilage tissue marker made of such a lysine oligomer derivative. A further objective is to provide a visualization reagent (composition) for a cartilage tissue which has a fluorescent group or a group for radiographic visualization.

MEANS FOR SOLVING PROBLEM

As a result of intense investigation to solve the above problems, we have found that a lysine oligomer which is an oligopeptide having a structure that an ε-amino group and a carboxyl group of lysines are linked via a peptide bond, can be a cartilage tissue marker. We have furthermore succeeded in visualizing a cartilage by binding a group capable of generating or absorbing electromagnetic wave to the above lysine oligomer, achieving the present invention.

Specifically, the present invention relates to a lysine oligomer derivative, wherein an ε-amino group and a carboxyl group of lysines are linked via a peptide bond, and a group capable of generating or absorbing electromagnetic wave is bonded to a C-terminal carboxyl group, an N-terminal amino group and/or an α-amino group.

Here, preferably 3 to 12 lysines are linked. Furthermore, the group capable of generating or absorbing electromagnetic wave is preferably a fluorescent group or a group for radiographic visualization. More preferably, the group capable of generating or absorbing electromagnetic wave is an iodine-containing group for radiographic visualization. A preferred embodiment of the present invention is a cartilage tissue marker made of such a lysine oligomer derivative.

EFFECTS OF THE INVENTION

An oligopeptide having a structure that a plurality of lysines are linked via a peptide bond between an ε-amino group and a carboxyl group has a property that it specifically accumulates in a cartilage matrix. A lysine oligomer derivative of the present invention in which group capable of generating or absorbing electromagnetic wave is bonded to such an oligopeptide is, therefore, useful as a cartilage tissue marker.

A cartilage tissue marker of the present invention allows for constructing a visualization system for a cartilage tissue by a fluorometric imaging device or an X-ray equipment in an experimental animal. The use of this system allows for time-course and quantitative evaluation of the amount of a cartilage matrix. It is, therefore, useful for detecting reduction in a cartilage matrix in rheumatoid arthritis, osteoarthritis, injury or the like, or increase in a cartilage matrix in cartilage tumor or the like. It is also useful for post-therapeutic followup of a cartilage disease. It is also useful as a means for evaluating the status of a cartilage in development of a therapeutic agent for a cartilage disease.

BRIEF DESCRIPTION OF THE DRAWINGS

FIG. 1 is staining image of a cartilage when Compounds A to C are used.
FIG. 2 is a staining image of a cartilage when Compounds 26 to 29 are used.
FIG. 3 is an X-ray CT image of a cartilage when Compound D is used.

MODE FOR CARRYING OUT THE INVENTION

A lysine oligomer derivative of the present invention has a structure that an ε-amino group and a carboxyl group of lysines are linked via a peptide bond. It has a distinctive characteristic that unlike a general polylysine in which an α-amino group and a carboxyl group is linked via a peptide bond, an ε-amino group and a carboxyl group is linked via a peptide bond. A lysine oligomer derivative having such a structure can be specifically bonded to a cartilage tissue. Although its mechanism is not clearly understood, it is assumed that α-amino groups uninvolved in a peptide bond which are arranged at proper intervals would contribute to increase in interaction with a sulfonic group contained in chondroitin sulfate as a component of a cartilage matrix.

There are no particular restrictions to the number of lysines constituting a lysine oligomer derivative of the present invention, but preferably 3 to 12 lysines are linked. If the lysine number is less than 3, binding ability to a cartilage tissue may be reduced. If the lysine number is more than 12, synthesis of such a derivative may be difficult and its molecular weight may be too large to be smoothly distributed in a tissue.

A lysine oligomer derivative of the present invention has a structure that a group capable of generating or absorbing electromagnetic wave is bonded to a C-terminal carboxyl group, an N-terminal amino group and/or an α-amino group. Introduction of such a group allows a cartilage tissue to be visualized.

A preferable chemical structure of a lysine oligomer derivative of the present invention is represented by formula (I).

visualization, and in the light of improved imaging ability an iodobenzene derivative, particularly a triiodobenzene derivative is suitably employed. Furthermore, in the present invention, an iodine-containing group introduced in a lysine oligomer desirably contains a cationic group such as a guanidino group and an amino group for recognizing an anionic side chain such as a sulfo group in chondroitin sulfate constituting a cartilage tissue.

A fluorescent group can be selected from those derived from a fluorescent substance (for example, fluorescent dye) with less affinity for other tissues around a cartilage. Fluorescent dyes known to the skilled in the art can be therefore, appropriately selected, except calcein which can stain a bone or Hoechst which can stain a cell nucleus or DNA. Examples of a fluorescent dye as a fluorescent substance described above include, but not limited to, benzofurazan dyes such as NBD, rhodamine dyes (for example, rhodamine, carboxy-X-rhodamine, carboxyrhodamine, tetraethylrhodamine, tetramethylrhodamine, Rhodamine Red and Rhodamine Green) as well as fluorescein dyes (for example, fluorescein, carboxynaphthofluorescein, tetrachlorofluorescein, tetrabromosulfonfluorescein), cyanine dyes (for example, Cy7, Cy5.5, Cy5, Cy3.5, Cy3 and other Cy dyes: GE Healthcare), Alexa Fluor series (for example, Alexa Fluor 790, Alexa Fluor 750, Alexa Fluor 700, Alexa Fluor 680, Alexa Fluor 647, Alexa Fluor 633, Alexa Fluor 594, Alexa Fluor 568, Alexa Fluor 555, Alexa Fluor 546, Alexa Fluor 532, Alexa

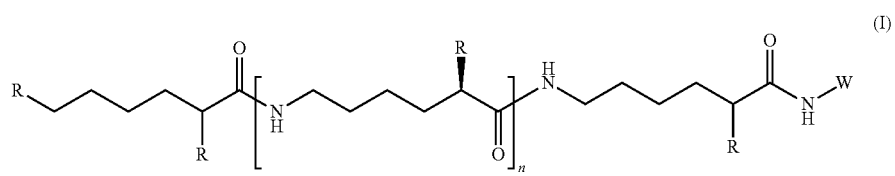

(I)

In formula (I), n is an integer of 1 to 10. In other words, the number of lysine units constituting the oligomer is 3 to 12. W is a group capable of generating or absorbing electromagnetic wave, preferably a fluorescent group or a group for radiographic visualization. Rs are independently of each other an amino group or a group capable of generating or absorbing electromagnetic wave. Therefore, all of Rs can be an amino group, or some can be an amino group while the others being a group capable of generating or absorbing electromagnetic wave, or alternatively all can be a group capable of generating or absorbing electromagnetic wave. R is preferably a fluorescent group or a group for radiographic visualization.

The phrase "group capable of generating or absorbing electromagnetic wave" as used herein refers to a group which can generate or absorb electromagnetic wave (electric wave, infrared ray, visual light, ultraviolet ray, X-ray, γ-ray or the like), allowing its existence to be imaged by macroscopic observation, a microscope, an imaging device or the like. Here, an example of a group capable of absorbing electromagnetic wave is a group for radiographic visualization, which can be imaged on the basis of attenuation of electromagnetic wave irradiated from the outside. An example of a group capable of generating electromagnetic wave is a fluorescent group, which can absorb higher energy to emit fluorescence, allowing for imaging.

It can be proposed that an iodine-containing group which absorbs much X-ray is used as a group for radiographic Fluor 488, Alexa Fluor 430, Alexa Fluor 405: INVITROGEN), VivoTag series (for example, VivoTag 5750, VivoTag 680, VivoTag S680: VisEn Medical), Atto dyes (for example, Atto 740, Atto 725, Atto 700, Atto 680, Atto 655, Atto 647, Atto 637, Atto 635, Atto 633, Atto 620, Atto 611X, Atto 610, Atto 594, Atto 590, Atto 565, Atto 550, Atto 532, Atto 520, Atto 495, Atto 488, Atto 465, Atto 425: ATTO-TEC GmbH), BODIPY dyes (for example, BODIPY 493/503, BODIPY 558/568, BODIPY 576/589, BODIPY 581/591, BODIPY TMR-X, BODIPY TR-X, BODIPY-530/550, BODIPY-FL-X), CAL Fluor dyes (for example, CAL Fluor-Gold 540, CAL Fluor Orange 560, CAL Fluor Red 590, CAL Fluor Red 610, CAL Fluor Red 635), Cascade Blue, Oregon Green dyes (for example, Oregon Green 488, Oregon Green 500, Oregon Green 514), Rhodol Green and Texas Red. An example of a fluorescent substance other than dyes is Qdot [nanocrystal phosphor utilizing photon emission from a quantum dot (several hundred to several thousand semiconductor atoms; for example, a mixture of cadmium with selenium or tellurium which is covered by a zinc sulfide shell and that which is further coated by a biopolymer are available): INVITROGEN].

There are no particular restrictions to a chemical synthetic process for a lysine oligomer derivative of the present invention. For example, it can be produced as described in Biopolymers, 1980, 19, 219-229 or by an appropriately modified process thereof. There will be described, but not limited to, exemplified synthetic processes.

(1) Preparation of a Lysine Oligomer

For example, a lysine oligomer in which an ε-amino group and a carboxyl group are bonded via a peptide bond can be prepared by starting a lysine derivative in which an ε-amino group is protected with a Z group (benzyloxycarbonyl group) or the like, an α-amino group is protected with a Boc group (tert-butoxycarbonyl group) and a carboxyl group is protected as methyl ester, which is treated with a condensing agent capable of forming a peptide bond to form a peptide. Then the resulting carboxylic acid ester can be deprotected by saponification with, for example, lithium hydroxide to provide a carboxylic-acid type of lysine oligomer.

(2) Introduction of a Group Capable of Generating or Absorbing Electromagnetic Wave To the carboxylic acid type thus obtained, a fluorescent group and a group for radiographic visualization or the like is introduced, and a Boc group can be removed using an acid to give a lysine oligomer derivative to which a group capable of generating or absorbing electromagnetic wave is bonded.

(3) Introduction of a Group for Radiographic Visualization

A de-Boc lysine oligomer described in (1) is reacted with an X-ray contrast agent including an iodine-containing benzoic acid derivative such as 3-iodo- or 3,5-diiodo-4-(2-guanidinoethylamino) benzoic acid, 3-iodo- or 3,5-diiodo-4-(2-aminoethylamino) benzoic acid and 2,3,5-triiodobenzoic acid or an amino-containing amide in which such an iodine-containing benzoic acid derivative and a diamine are bonded via a peptide bond in the presence of a common condensing agent for peptide synthesis, to provide an X-ray imageable lysine oligomer derivative. A cationic X-ray contrast agent used herein can be prepared by reductive aminoalkylation of an amino group in an aminobenzoate as a starting material, guanidinylation of a terminal amino group and then a reaction with iodine in the presence of silver sulfate in methanol.

A lysine oligomer derivative of the present invention can be a pharmaceutically acceptable salt. When isomers (for example, optical isomers, geometric isomers and tautomers) exist, the present invention encompasses these isomers, and furthermore solvates, hydrates and various types of crystals. In the present invention, a pharmaceutically acceptable salt is a pharmacologically and pharmaceutically acceptable salt, particularly an acid addition salt including an inorganic salt such as a hydrochloride, a sulfate, a nitrate, a phosphate, a carbonate, a bicarbonate and a perchlorate.

A lysine oligomer in which an ε-amino group and a carboxyl group are bonded via a peptide bond can be specifically bonded to a cartilage tissue, and can, therefore, act as a marker for the cartilage tissue. Therefore, a lysine oligomer derivative of the present invention to which a group capable of generating or absorbing electromagnetic wave such as a fluorescent group or a group for radiographic visualization is introduced can be used as a cartilage tissue visualization reagent which can be easily detected by a method such as fluorescence microscopy, optical projection tomography and X-ray photography.

A cartilage tissue marker of the present invention is dissolved in a sterilized aqueous medium (particularly, water, saline, buffered saline or the like) to prepare a composition, which can be used as a visualization reagent for a cartilage tissue. A concentration in the composition can be determined as appropriate. As a non-limiting example, a composition with a concentration of 0.01 mM to 1 mM can be administered into a joint cavity in a proper amount.

As described above, a lysine oligomer in which an ε-amino group and a carboxyl group are linked via a peptide bond selectively accumulates in a cartilage. This was verified using a lysine oligomer derivative to which a group capable of generating or absorbing electromagnetic wave is bonded, as described in Examples below. This lysine oligomer can be, therefore, used as a carrier for delivering a drug to the targeted cartilage. That is, a drug prepared by bonding a pharmaceutical ingredient for cartilage treatment to a lysine oligomer in which an ε-amino group and a carboxyl group are linked via a peptide bond can be administered (for example, into a joint cavity) to efficiently accumulate in a cartilage. Here, for determining accumulation of the drug in a cartilage, a group capable of generating or absorbing electromagnetic wave can be bonded, but such a group may be absent.

A lysine oligomer with ε-bond linkage of the present invention is specifically bonded to a cartilage tissue. Therefore, it can be bonded to a group capable of generating or absorbing electromagnetic wave such as a fluorescent group or a group for radiographic visualization, and the product allows a cartilage tissue to be visualized and thus, is useful as a means for evaluating the status of a cartilage in developing a therapeutic agent for a cartilage disease. Furthermore, the lysine oligomer is also useful as a means for selectively delivering a therapeutic agent to a cartilage.

EXAMPLES

Syntheses of Lysine Oligomer Derivatives

1) Synthesis of Intermediate 2

Nα-(tert-butoxycarbonyl)-L-lysine (1) (985 mg, 4 mmol) was dissolved in anhydrous 1,4-dioxane (3 mL) and water (3 mL). After adding triethylamine (615 μL, 4.4 mmol), to the solution was added di-tert-butyl dicarbonate (960 mg, 4.4 mmol) dropwise under ice-cooling, and then the mixture was stirred for 18 hours. Completion of the reaction was confirmed by TLC (ethyl acetate:n-hexane=5:1), and the reaction solution was poured into a 0.5 N aqueous solution of hydrochloric acid (80 mL). The mixture was extracted with ethyl acetate (3×40 mL) and the organic layer was washed with saturated saline (80 mL) and dried over anhydrous magnesium sulfate. After evaporation under a reduced pressure, the obtained material was purified by flash column chromatography (ethyl acetate:n-hexane=1:1 to 2:1) to give intermediate 2 (1.29 g, 93%) as a white solid.

$^1$H-NMR (300 MHz, CDCl$_3$) δ: 5.21(br s, 1H), 4.62(br s, 1H), 4.28(br s, 1H), 3.14(d, 2H, J=6.0 Hz), 1.88(br s, 1H), 1.76(br s, 1H), 1.45-1.23(m, 22H), 0.92-0.88(m, 1H).

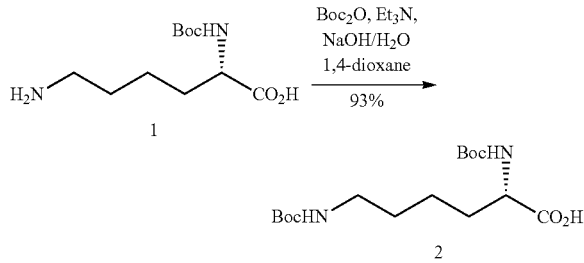

2) Synthesis of Intermediate 4

Under an Ar atmosphere, Nα-(tert-butoxycarbonyl)-Nε-(benzyloxycarbonyl)-L-lysine (3) (810 mg, 2.1 mmol) was dissolved in anhydrous DMF (2 mL) and anhydrous methanol (1 mL). To the solution were sequentially added 1-hydroxybenzotriazole monohydrate (390 mg, 2.6 mmol) and 1-(3-dimethylaminopropyl)-3-ethylcarbodiimide hydrochloride (490 mg, 2.6 mmol), and the mixture was ice-cooled and stirred for 2 hours. After confirming completion of the reaction by TLC (ethyl acetate alone), the reaction solution was poured into water and extracted with ethyl acetate (3×70 mL). The organic layer was washed with a saturated aqueous sodium hydrogen carbonate solution (70 mL), water (70 mL) and then saturated saline (70 mL), and dried over anhydrous magnesium sulfate. After evaporation under a reduced pressure, the obtained material was purified by flash column chromatography (ethyl acetate:n-hexane=1:4 to 1:2), to give intermediate 4 (839 mg, 99%) as a colorless oil.

$^1$H-NMR (300 MHz, CDCl$_3$) δ: 7.36-7.33(m, 5H), 5.09(s, 2H), 5.06(s, 1H), 4.81(s, 1H), 3.73(s, 3H), 3.20(q, 2H, J=6.5 Hz), 1.77-1.67(m, 2H), 1.53-1.51(m, 2H), 1.42-1.37(m, 11H).

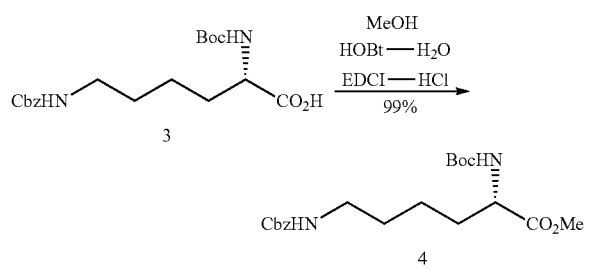

3) Synthesis of Intermediate 5

Intermediate 4 (839 mg, 2.1 mmol) was dissolved in methanol (15 mL). After adding Pd/C (catalytic amount), the mixture was stirred under hydrogen atmosphere at room temperature for 40 min. After confirming completion of the reaction by TLC (ethyl acetate:n-hexane=2:1), the reaction solution was filtered through a Celite pad. After evaporation under a reduced pressure, intermediate 5 (563 mg, q.y.) was obtained as a colorless oil, which was used as such in the next reaction.

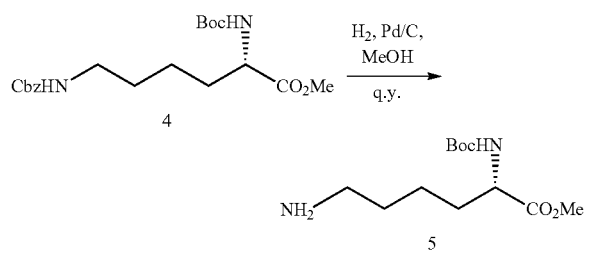

4) Synthesis of Intermediate 6

Under an Ar atmosphere, intermediate 5 (560 mg, 2.2 mmol), Nα-(tert-butoxycarbonyl)-Nε-(benzyloxycarbonyl)-L-lysine (837 mg, 2.2 mmol) (3) were dissolved in anhydrous DMF (10 mL). To the solution was sequentially added 1-hydroxybenzotriazole monohydrate (337 mg, 2.2 mmol) and 1-(3-dimethylaminopropyl)-3-ethylcarbodiimide hydrochloride (423 mg, 2.2 mmol), and the mixture was ice-cooled and stirred for 5.5 hours. After confirming completion of the reaction by TLC (ethyl acetate:n-hexane=3:1), the reaction solution was poured into water. The mixture was extracted with ethyl acetate (3×70 mL), and the organic layer was washed with a saturated aqueous sodium hydrogen carbonate solution (70 mL), water (70 mL) and saturated saline (70 mL) and then dried over anhydrous magnesium sulfate. After evaporation under a reduced pressure, intermediate 6 (596 mg, 44%) was obtained as a white solid.

$^1$H-NMR (300 MHz, CDCl$_3$) δ: 7.36(br s, 5H), 6.18(br s, 1H), 5.19(br s, 2H), 5.10(s, 2H), 4.90(br s, 1H), 4.25(br s, 1H), 4.00(br s, 1H), 3.73(s, 3H), 3.21(br s, 4H), 1.83(br s, 2H), 1.44(d, 18H, J=3.0 Hz).

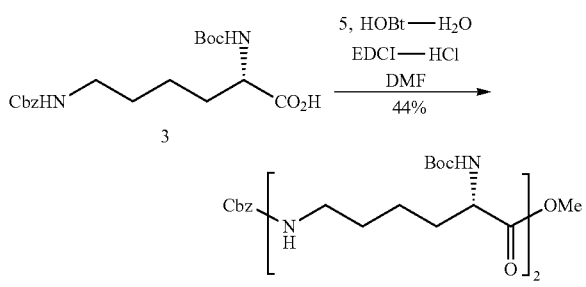

5) Synthesis of Intermediate 7

Intermediate 6 (790 mg, 1.3 mmol) was dissolved in THF:water=3:2 (32 mL). To the solution was added lithium hydroxide monohydrate (161 mg, 3.8 mmol), and the mixture was stirred at room temperature for 2 hours. After confirming completion of the reaction by TLC (ethyl acetate), the reaction solution was poured into a saturated aqueous ammonium chloride solution (50 mL), and the mixture was extracted with ethyl acetate (3×30 mL), and the organic layer was washed with saturated saline (2×50 mL) and then dried over anhydrous magnesium sulfate. After evaporation under a reduced pressure, colorless and viscous intermediate 7 (840 mg, q.y.) was obtained, which was used as such in the next reaction.

Rf=0.48 (CH$_2$Cl$_2$:MeOH=1:2); $^1$H-NMR (300 MHz, CDCl$_3$) δ: 7.34(br s, 5H), 5.14(br s, 1H), 5.09(s, 2H), 4.16-3.84(m, 3H), 3.18(br s, 3H), 1.97-1.90(m, 1H), 1.77(br s, 2H), 1.63-1.21(m, 5H), 1.51(s, 4H), 1.44-1.40(m, 18H).

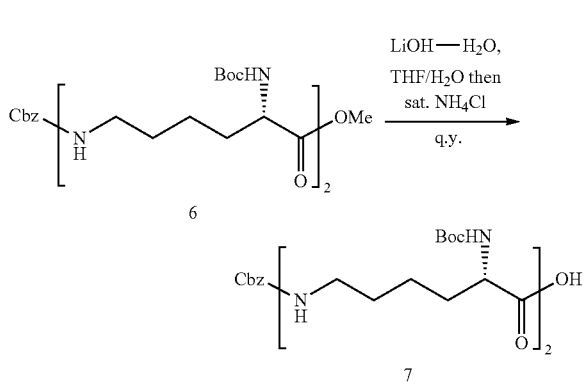

6) Synthesis of Intermediate 8

Intermediate 6 (595 mg, 1.0 mmol) was dissolved in methanol (13 mL). After adding Pd/C (catalytic amount), the mixture was stirred under hydrogen atmosphere, at room temperature for 7.5 hours. After confirming completion of the reaction by a TLC (ethyl acetate), the reaction solution was filtered through a Celite pad. After evaporation under a reduced pressure, intermediate 8 (469 mg, q.y.) was obtained as a white solid, which was used as such in the next reaction.

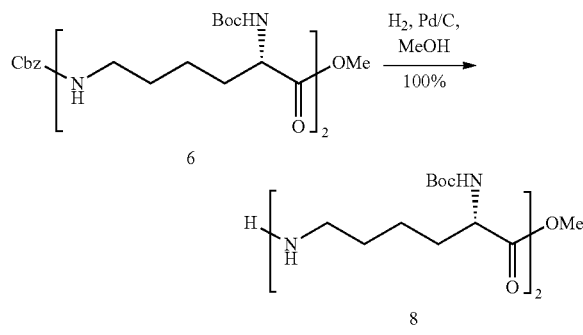

7) Synthesis of Intermediate 9

Under an Ar atmosphere, intermediate 8 (376 mg, 0.77 mmol) and Nα-(tert-butoxycarbonyl)-Nε-(benzyloxycarbonyl)-L-lysine (3) (293 mg, 0.77 mmol) were dissolved in anhydrous DMF (5 mL). To the solution were sequentially added 1-hydroxybenzotriazole monohydrate (141 mg, 0.92 mmol) and 1-(3-dimethylaminopropyl)-3-ethylcarbodiimide hydrochloride (176 mg, 0.92 mmol), and the mixture was ice-cooled and stirred for 4 hours. After confirming completion of the reaction by TLC (ethyl acetate alone), the reaction solution was poured into a saturated aqueous sodium hydrogen carbonate solution (50 mL). The mixture was extracted with ethyl acetate (3×50 mL), and the organic layer was washed with saturated saline (100 mL) and then dried over anhydrous magnesium sulfate. After evaporation under a reduced pressure, the obtained material was purified by flash column chromatography (ethyl acetate:n-hexane=1:3), to give intermediate 9 (504 mg, 77%) as a white foamy solid.

$^1$H-NMR (300 MHz, CDCl$_3$) δ: 7.35(br s, 5H), 6.47(br s, 2H), 5.37-5.05(m, 6H), 4.23(br s, 1H), 4.00(br s, 2H), 3.73(s, 3H), 3.21(t, J=6.5 Hz, 6H), 1.80(br s, 3H), 1.71-1.24 (m, 13H), 1.43(d, J=3.5 Hz, 27H).

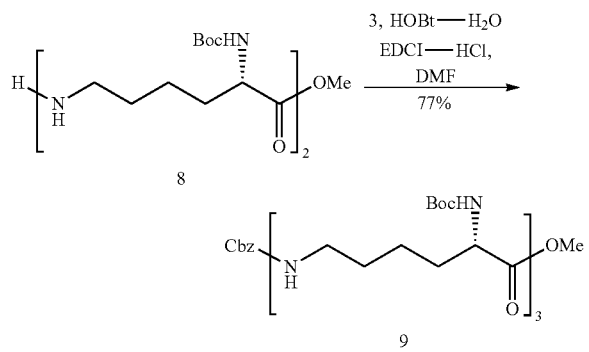

8) Synthesis of Intermediate 10

Under an Ar atmosphere, intermediate 8 (255 mg, 0.52 mmol) and intermediate 7 (319 mg, 0.52 mmol) were dissolved in anhydrous DMF (5 mL). To the solution were sequentially added 1-hydroxybenzotriazole monohydrate (96 mg, 0.62 mmol) and 1-(3-dimethylaminopropyl)-3-ethylcarbodiimide hydrochloride (119 mg, 0.62 mmol), and the mixture was ice-cooled and stirred for 2 hours. After confirming completion of the reaction by TLC (methylene chloride:methanol=9:1), the reaction solution was poured into water (50 mL). The mixture was extracted with ethyl acetate (3×50 mL), and the organic layer was washed with water (100 mL) and saturated saline (100 mL) and then dried over anhydrous magnesium sulfate. After evaporation under a reduced pressure, the obtained material was purified by flash column chromatography (ethyl acetate:n-hexane=9:1), to give intermediate 10 (464 mg, 83%) as a white solid.

$^1$H-NMR (300 MHz, CDCl$_3$) δ: 7.42-7.29(m, 5H), 6.59(br s, 1H), 6.50(br s, 1H), 5.61-5.17(m, 4H), 5.10(s, 2H), 4.24(br s, 1H), 4.00(br s, 3H), 3.73(s, 3H), 3.32(br s, 2H), 3.27-3.17(m, 6H), 1.79-1.35(m, 24H), 1.45-1.41(m, 36H).

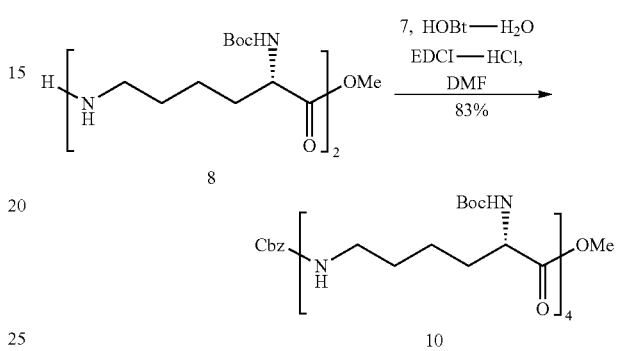

9) Synthesis of Intermediate 11

Intermediate 9 (504 mg, 0.6 mmol) was dissolved in methanol (5 mL). After adding Pd/C (catalytic amount), the mixture was stirred under hydrogen atmosphere at room temperature for 1.5 hours. After confirming completion of the reaction by TLC (ethyl acetate), the reaction solution was filtered through a Celite pad. After evaporation under a reduced pressure, intermediate 11 (421 mg, 99%) was obtained as a white foamy solid, which was used as such in the next reaction.

$^1$H NMR (300 MHz, CDCl$_3$) δ: 6.57(br s, 1H), 6.50(br s, 1H), 5.44(br s, 1H), 5.26(br s, 2H), 4.23(br s, 1H), 4.07-3.93(m, 2H), 3.73(s, 3H), 3.24(d, J=5.0 Hz, 4H), 2.71(t, J=6.5 Hz, 2H), 1.81(br s, 3H), 1.65(br s, 3H), 1.59-1.46(m, 7H), 1.44-1.43(m, 27H), 1.40-1.39(m, 7H).

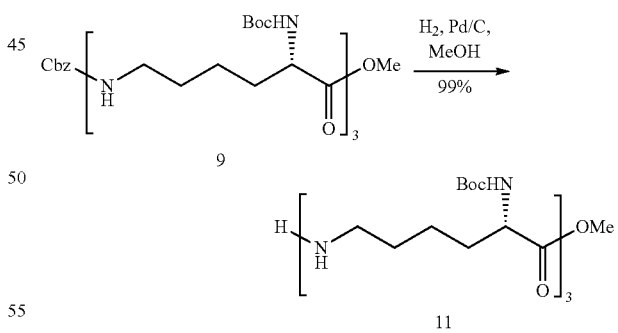

10) Synthesis of Intermediate 12

Intermediate 10 (446 mg, 0.41 mmol) was dissolved in methanol (5 mL). After adding Pd/C (catalytic amount), the mixture was stirred under hydrogen atmosphere at room temperature for 0.5 hours. After confirming completion of the reaction by TLC (ethyl acetate), the reaction solution was filtered through a Celite pad. After evaporation under a reduced pressure, intermediate 12 (392 mg, 95%) was obtained as a white foamy solid, which was used as such in the next reaction.

¹H-NMR (300 MHz, CDCl₃) δ: 6.97(br s, 1H), 5.60-5.49 (m, 3H), 4.22(br s, 1H), 4.16-3.98(m, 3H), 3.73(s, 3H), 3.23(br s, 5H), 2.74(br s, 2H), 1.82(br s, 20H), 1.70-1.22(m, 7H), 1.44-1.43(m, 36H).

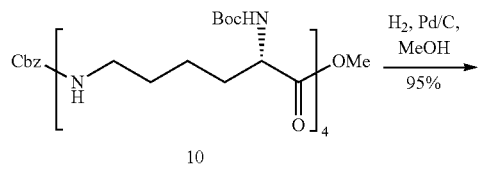

11) Synthesis of Intermediate 13

Under an Ar atmosphere, intermediate 8 (469 mg, 1.0 mmol) and intermediate 2 (360 mg, 1.0 mmol) were dissolved in anhydrous DMF (8 mL). To the solution were sequentially added 1-hydroxybenzotriazole monohydrate (176 mg, 1.2 mmol) and 1-(3-dimethylaminopropyl)-3-ethylcarbodiimide hydrochloride (220 mg, 1.2 mmol), and the mixture was ice-cooled and stirred for 13 hours. After confirming completion of the reaction by TLC (ethyl acetate), the reaction solution was poured into water. The mixture was extracted with ethyl acetate (3×90 mL) and the organic layer was washed with water (2×90 mL) and saturated saline (90 mL) and then dried over anhydrous magnesium sulfate. After evaporation under a reduced pressure, the obtained material was purified by flash column chromatography (ethyl acetate:n-hexane=2:1 to 1:0), to give intermediate 13 (166 mg, 21%) as a yellow solid.

¹H-NMR (300 MHz, CDCl₃) δ: 6.45-6.37(m, 2H), 5.27(br s, 1H), 4.71(br s, 1H), 4.25(br s, 1H), 4.90(br s, 1H), 4.25(br s, 1H), 4.01(br s, 2H), 3.74(s, 3H), 3.25(br s, 3H), 3.12(br s, 2H), 1.80(br s, 3H), 1.69-1.64(m, 4H), 1.45(s, 36H).

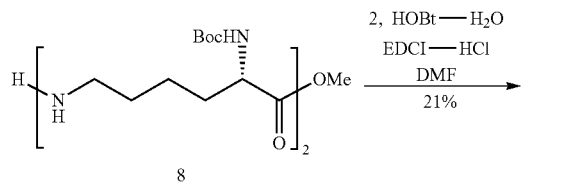

12) Synthesis of Intermediate 14

Under an Ar atmosphere, intermediate 11 (143 mg, 0.2 mmol) and intermediate 2 (69 mg, 0.2 mmol) were dissolved in anhydrous DMF (3 mL). To the solution were sequentially added 1-hydroxybenzotriazole monohydrate (37 mg, 0.24 mmol) and 1-(3-dimethylaminopropyl)-3-ethylcarbodiimide hydrochloride (46 mg, 0.24 mmol), and the mixture was ice-cooled and stirred for 14 hours. After confirming completion of the reaction by TLC (ethyl acetate), the reaction solution was poured into water (50 mL). The mixture was extracted with ethyl acetate (3×30 mL), and the organic layer was washed with water (70 mL) and saturated saline (70 mL), and then dried over anhydrous magnesium sulfate. After evaporation under a reduced pressure, the obtained material was purified by flash column chromatography (methylene chloride:methanol=19:1), to give intermediate 14 (118 mg, 56%) as a white solid.

Rf=0.57 (CH₂Cl₂:MeOH=9:1); ¹H-NMR (300 MHz, CDCl₃) δ: 5.47(br s, 1H), 4.24(br s, 1H), 4.00(br s, 2H), 3.31-3.17(m, 7H), 1.81(br s, 4H), 1.61-1.43(m, 14H), 1.43 (d, J=3.5 Hz, 45H).

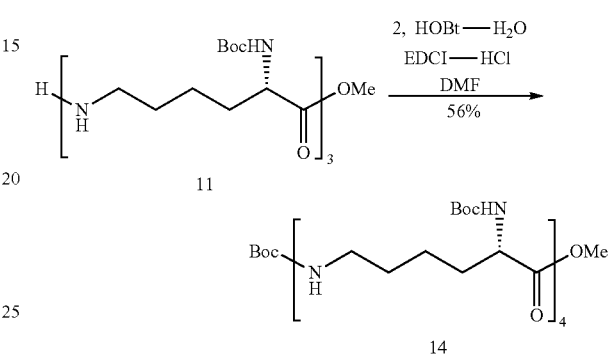

13) Synthesis of Intermediate 15

Under an Ar atmosphere, intermediate 12 (189 mg, 0.20 mmol) and intermediate 2 (69.3 mg, 0.20 mmol) were dissolved in anhydrous DMF (3 mL). To the solution were sequentially added 1-hydroxybenzotriazole monohydrate (36.8 mg, 0.24 mmol) and 1-(3-dimethylaminopropyl)-3-ethylcarbodiimide hydrochloride (46.0 mg, 0.24 mmol), and the mixture was ice-cooled and stirred for 20 hours. After confirming completion of the reaction by TLC (methylene chloride:methanol=9:1), the reaction solution was poured into a saturated aqueous ammonium chloride solution (50 mL). The mixture was extracted with ethyl acetate (3×50 mL), and the organic layer was washed with water (100 mL) and saturated saline (100 mL) and then dried over anhydrous magnesium sulfate. After evaporation under a reduced pressure, the obtained material was purified by flash column chromatography (ethyl acetate), to give intermediate 15 (235 mg, 92%) as a white solid.

Rf=0.51 (CH₂Cl₂:MeOH=9:1); ¹H-NMR (300 MHz, CDCl₃) δ: 7.14(s, 1H), 6.79(s, 1H), 6.58(s, 1H), 5.75(br s, 1H), 5.51(br s, 2H), 5.41(br s, 1H), 4.89(br s, 1H), 4.21(br s, 3H), 4.01(br s, 2H), 3.41(br s, 3H), 3.22(br s, 3H), 3.11(d, J=6.0 Hz), 1.77-0.90(m, 35H), 1.43(t, J=2.0 Hz, 36H), 1.42(s, 18H).

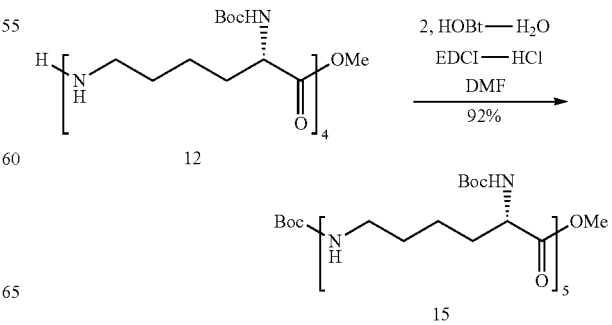

14) Synthesis of Intermediate 16

Intermediate 13 (90 mg, 0.11 mmol) was dissolved in THF:water=3:1 (5.5 mL). After adding lithium hydroxide monohydrate (28 mg, 0.66 mmol), the mixture was stirred at room temperature for 1 hour. After confirming completion of the reaction by TLC (ethyl acetate), the reaction solution was poured into a saturated aqueous ammonium chloride solution (20 mL). The mixture was extracted with ethyl acetate (3×30 mL) and the organic layer was washed with saturated saline (50 mL) and then dried over anhydrous magnesium sulfate. After evaporation under a reduced pressure, colorless and viscous intermediate 16 (83 mg, 94%) was obtained, which was used as such in the next reaction.

$^1$H-NMR (300 MHz, CDCl$_3$) δ: 5.45(br s, 2H), 4.84(br s, 1), 4.23-3.84(m, 3H), 3.17(br s, 5H), 0.94-0.19(m, 14H), 1.80(br s, 2H), 1.43(s, 36H). FAB-MS m/e: 804[M+H]$^+$

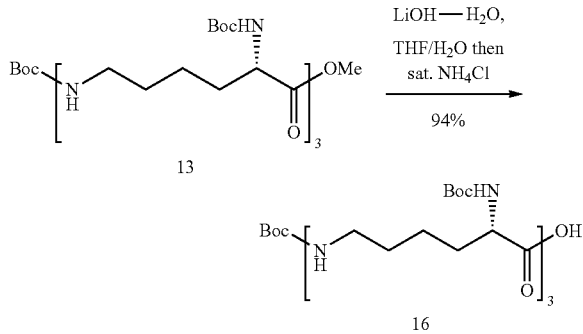

15) Synthesis of Intermediate 17

Intermediate 14 (180 mg, 0.17 mmol) was dissolved in THF:water=3:2 (1 mL). After adding lithium hydroxide monohydrate (43 mg, 1.0 mmol), the mixture was stirred at room temperature for 2 hours. After confirming completion of the reaction by TLC (ethyl acetate), the reaction solution was poured into a 0.5 N aqueous hydrochloric acid solution (40 mL). The mixture was extracted with ethyl acetate (3×40 mL), and the organic layer was washed with water (2×40 mL) and saturated saline (40 mL) and then dried over anhydrous magnesium sulfate. After evaporation under a reduced pressure, intermediate 17 (160 mg, 92%) was obtained as a white solid, which was used as such in the next reaction.

Rf=0.49 (CH$_2$Cl$_2$:MeOH=9:1); $^1$H-NMR (300 MHz, CDCl$_3$) δ: 5.39(br s, 2H), 4.05(br s, 2H), 3.10(d, J=5.0 Hz, 2H), 1.80(br s, 5H), 1.56(br s, 7H), 1.44-1.24(m, 9H), 1.44(d, J=4.0 Hz, 45H).

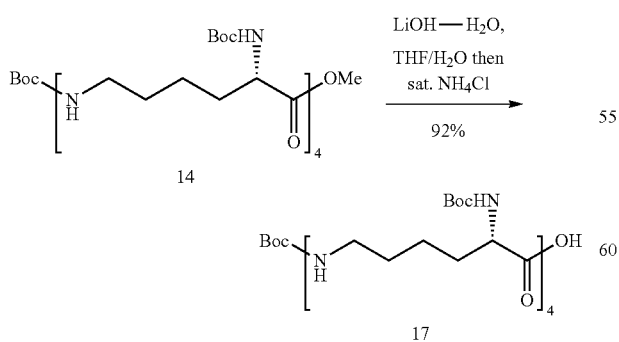

16) Synthesis of Intermediate 18

Intermediate 15 (190 mg, 0.15 mmol) was dissolved in THF:water=3:2 (18 mL). After adding lithium hydroxide monohydrate (89 mg, 2.1 mmol), the mixture was stirred at room temperature for 2 hours. After confirming completion of the reaction by TLC (ethyl acetate), the reaction solution was poured into a saturated aqueous ammonium chloride solution (50 mL). The mixture was extracted with ethyl acetate (3×50 mL), and the organic layer was washed with saturated saline (2×50 mL) and then dried over anhydrous magnesium sulfate. After evaporation under a reduced pressure, colorless and viscous intermediate 18 (210 mg, q.y.) was obtained, which was used as such in the next reaction.

Rf=0.48 (CH$_2$Cl$_2$:MeOH=1:2); $^1$H-NMR (300 MHz, CDCl$_3$) δ: 5.61-5.50(m, 2H), 4.36-3.68(m, 6H), 3.48(d, J=5.0 Hz, 2H), 3.09(br s, 6H), 2.26-0.86(m, 29H), 1.43(br s, 54H).

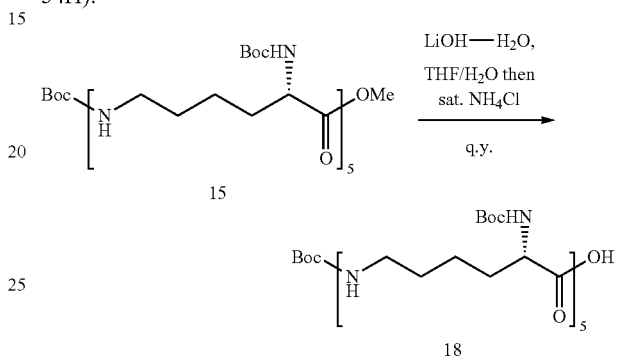

17) Synthesis of Intermediate 20

Under an Ar atmosphere, 4-chloro-7-nitrobenzofurazan (NBD-Cl: 19) (99.4 mg, 0.5 mmol) was dissolved in anhydrous DMF (3 mL). After adding triethylamine (69 µL, 0.5 mmol) and N-(tert-butoxycarbonyl)-1,2-diaminoethane (87 µL, 0.6 mmol), the mixture was stirred at room temperature for 2 hours. After confirming completion of the reaction by TLC (ethyl acetate:n-hexane=1:1), the reaction solution was poured into a saturated aqueous ammonium chloride solution (20 mL). The mixture was extracted with ethyl acetate (3×30 mL), and the organic layer was washed with water (50 mL) and saturated saline (50 mL) and then dried over anhydrous magnesium sulfate. After evaporation under a reduced pressure, brown-green and oily intermediate 20 (171 mg, q.y.) was obtained.

$^1$H-NMR (300 MHz, CDCl$_3$) δ: 8.51(d, 1H, J=9.0 Hz), 7.70(br s, 1H), 6.17(d, 1H, J=9.0 Hz), 5.08(br s, 1H), 3.61(br s, 4H), 1.47(s, 9H).

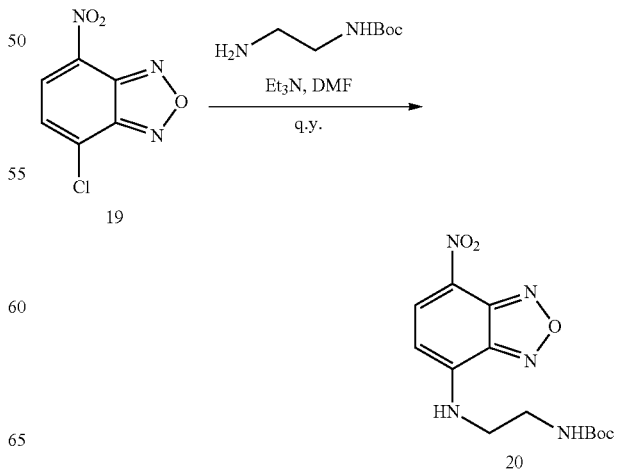

18) Synthesis of Intermediate 21

Under an Ar atmosphere, intermediate 20 (90 mg, 0.28 mmol) was dissolved in a 4.0 N solution of hydrogen chloride in 1,4-dioxane (2 mL). The solution was shaded from the light and stirred for 5.5 hours. After confirming completion of the reaction by TLC (methylene chloride:methanol=29:1), the reaction solution was air-dried. After evaporation under a reduced pressure, the obtained material was recrystallized from methanol/ethyl acetate to give intermediate 21 (68 mg, 94%) as a red-brown solid.

$^1$H-NMR (300 MHz, CD$_3$OD) δ: 8.56(d, 1H, J=9.0 Hz), 6.46(d, 1H, J=9.0 Hz), 3.87(t, 2H, J=6.0 Hz), 3.34(br s, 2H).

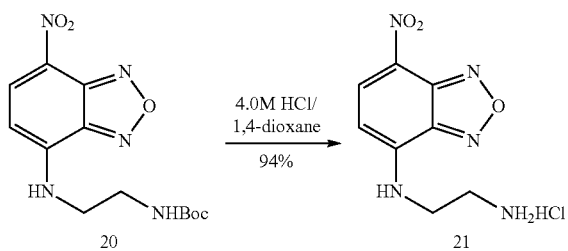

19) Synthesis of Intermediate 22 (Kε1-Boc)

Under an Ar atmosphere, intermediate 2 (100 mg, 0.3 mmol) was dissolved in anhydrous DMF. To the solution were sequentially added 1-hydroxybenzotriazole monohydrate (55 mg, 0.36 mmol), 1-(3-dimethylaminopropyl)-3-ethylcarbodiimide hydrochloride (69 mg, 0.36 mmol) and intermediate 21 (78 mg, 0.30 mmol) under ice-cooling, and the mixture was shaded from the light, allowed to be warmed to room temperature, and stirred for 2 hours. After confirming completion of the reaction by TLC (methylene chloride:methanol=9:1), the reaction solution was poured into a 0.5M aqueous hydrochloric acid solution (40 mL). The mixture was extracted with ethyl acetate (3×40 mL), and the organic layer was washed with water (2×40 mL) and saturated saline (40 mL) and then dried over anhydrous magnesium sulfate. After evaporation under a reduced pressure, the obtained material was purified by flash column chromatography (n-hexane:ethyl acetate=1:1 to 1:5), to give intermediate 22 (110 mg, 67%) as a yellow solid.

$^1$H-NMR (300 MHz, CD-OD) δ: 6.43(d, J=9.0 Hz, 1H), 3.90(b/s, 1H), 3.66(br s, 2H), 3.55(br s, 2H), 2.97(t, J=5.5 Hz, 2H), 1.63(br s, 1H), 3.66(br s, J=2.0 Hz, 18H).

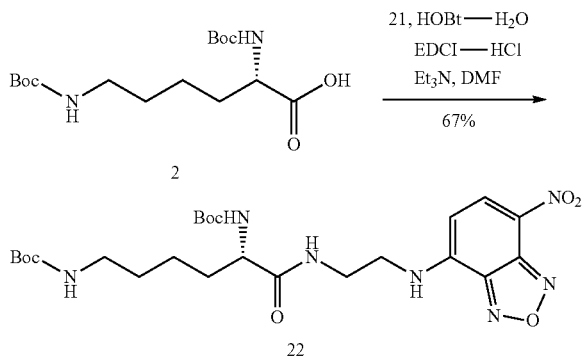

20) Synthesis of Intermediate 23 (Kε3-Boc)

Under an Ar atmosphere, intermediate 16 (73.9 mg, 0.092 mmol) was dissolved in anhydrous DMF, and triethylamine (26 μL, 0.184 mmol) was added. Under ice-cooling, 1-hydroxybenzotriazole monohydrate (16.8 mg, 0.110 mmol), 1-(3-dimethylaminopropyl)-3-ethylcarbodiimide hydrochloride (21.1 mg, 0.110 mmol) and intermediate 21 (23.9 mg, 0.092 mmol) were sequentially added. The mixture was shaded from the light, allowed to be warmed to room temperature, and stirred 20 hours. After confirming completion of the reaction by TLC (methylene chloride:methanol=9:1), the reaction solution was poured into a saturated aqueous sodium hydrogen carbonate solution (30 mL). The mixture was extracted with ethyl acetate (3×30 mL), and the organic layer was washed with a saturated aqueous ammonium chloride solution (50 mL) and saturated saline (50 mL) and then dried over anhydrous magnesium sulfate. After evaporation under a reduced pressure, the obtained material was purified by flash column chromatography (methylene chloride:n-hexane:ethyl acetate:methanol=9:5:4:1), to give intermediate 23 (74.8 mg, 81%) as an orange foamy solid.

$^1$H-NMR (300 MHz, CDCl$_3$) δ: 8.51(d, 1H, J=8.5 Hz), 8.12(br s, 1H), 7.66(br s, 1H), 6.65(br s, 1H), 6.44(br s, 1H), 6.21(d, 1H, J=8.5 Hz), 5.60(br s, 1H), 5.48(br s, 2H), 4.75(br s, 1H), 4.00(br s, 2H), 3.67(br s, 3H), 3.26(br s, 1H), 1.82(br s, 3H), 1.43(s, 36H).

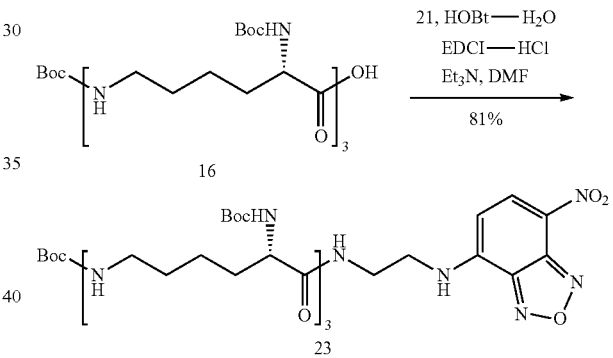

21) Synthesis of Intermediate 24 (Kε4-Boc)

Under an Ar atmosphere, intermediate 17 (119 mg, 0.12 mmol) and intermediate 21 (31 mg, 0.12 mmol) were dissolved in anhydrous DMF (3 mL), and triethylamine (33 μL, 0.24 mmol) was added. Under ice-cooling, 1-hydroxybenzotriazolemonohydrate (21 mg, 0.14 mmol) and 1-(3-dimethylaminopropyl)-3-ethylcarbodiimide hydrochloride (27 mg, 0.14 mmol) were sequentially added, and the solution was shaded from the light, allowed to be warmed to room temperature and stirred for 8 hours. After confirming completion of the reaction by TLC (methylene chloride:methanol=19:1), the reaction solution was poured into a saturated aqueous sodium hydrogen carbonate solution (50 mL). The mixture was extracted with ethyl acetate (3×50 mL), and the organic layer was washed with a saturated aqueous ammonium chloride solution (50 mL), water (50 mL) and saturated saline (50 mL) and then dried over anhydrous magnesium sulfate. After evaporation under a reduced pressure, the obtained material was purified by flash column chromatography (methylene chloride:methanol=29:1 to 9:1), to give intermediate 24 (113.4 mg, 79%) as an orange foamy solid.

Rf=0.55 (CH$_2$Cl$_2$:MeOH=9:1); $^1$H-NMR (300 MHz, CDCl$_3$) δ: 8.49(d, J=8.5 Hz, 1H), 8.13(br s, 1H), 6.90(br s, 1H), 6.49(br s, 1H), 6.19(d, J=8.5 Hz, 1H), 5.78(br s, 1H), 5.41(br s, 1H), 4.76(br s, 1H), 4.23-4.02(m, 1H), 3.67(br s, 3H), 3.48(br s, 3H), 3.10(br s, 3H), 1.79(q, J=12.5 Hz, 45H), 1.71-1.17(m, 32H), 1.41(br s, 2H); [α]$_D$ +14.4° (c=1.0083, MeOH).

$^1$H-NMR (300 MHz, CDCl$_3$) δ: 8.49(d, J=8.5 Hz, 1H), 8.22(br s, 1H), 6.19(d, J=8.5 Hz, 1H), 4.81(br s, 1H), 4.05(br s, 5H), 3.68(br s, 4H), 3.49(br s, 4H), 3.10(br s, 6H), 1.83-1.11(m, 28H), 1.42(t, J=5.0 Hz, 54H); [α]$_D$ +21.7° (c=1.0108, MeOH).

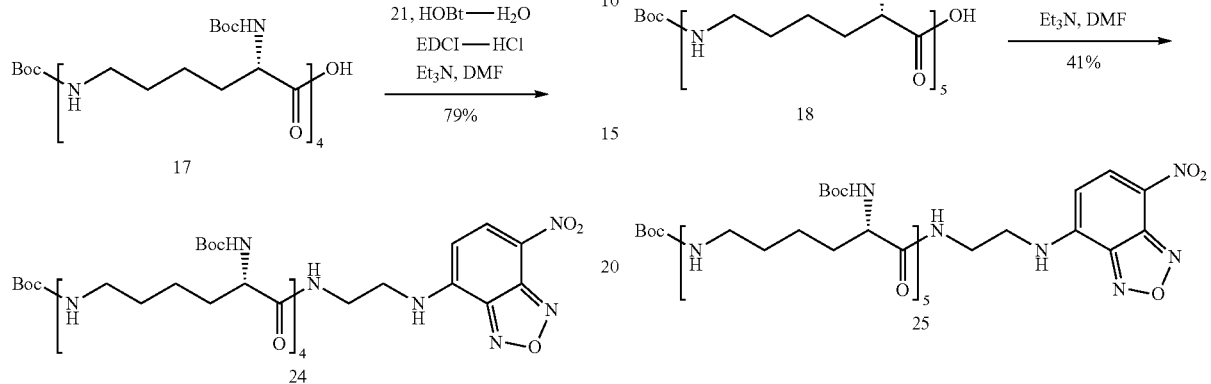

22) Synthesis of Intermediate 25 (Kε5-Boc)

Under an Ar atmosphere, intermediate 18 (168 mg, 0.13 mmol) and intermediate 21 (34.6 mg, 0.13 mmol) were dissolved in anhydrous DMF (3 mL) and triethylamine (36 μL, 0.26 mmol) was added. To the solution were sequentially added 1-hydroxybenzotriazole monohydrate (24.5 mg, 0.16 mmol) and 1-(3-dimethylaminopropyl)-3-ethylcarbodiimide hydrochloride (30.7 mg, 0.16 mmol) under ice-cooling, and the mixture was shaded from the light, allowed to be warmed to room temperature and stirred for 17.5 hours. After confirming completion of the reaction by TLC (methylene chloride:methanol=19:1), the reaction solution was poured into a saturated aqueous sodium hydrogen carbonate solution (50 mL). The mixture was extracted with ethyl acetate (3×50 mL), and the organic layer was washed with a saturated aqueous ammonium chloride solution (50 mL), water (50 mL) and saturated saline (50 mL) and then dried over anhydrous magnesium sulfate. After evaporation under a reduced pressure, the obtained material was purified by flash column chromatography (methylene chloride:methanol=29:1 to 9:1), to give intermediate 25 (77.4 mg, 41%) as an orange foamy solid.

23) Synthesis of a Target Compound 26 (Kε1-NBD)

Under an Ar atmosphere, intermediate 22 (83 mg, 0.15 mmol) was dissolved in anhydrous methanol (2 mL) and a 4.0 N solution of hydrochloric acid in 1,4-dioxane (2 mL), and the solution was shaded from the light and stirred for 2 hours. After confirming completion of the reaction by TLC (methylene chloride:methanol=9:1), the reaction solution was air-dried. After evaporation under a reduced pressure, the material was recrystallized from methanol/ethyl acetate to give a target compound 26 (Kε1-NBD) (25 mg, 40%) as a red solid.

m.p. 151.4-153.9° C.; $^1$H-NMR (300 MHz, CD$_3$OD) 8.55(d, J=9.0 Hz, 1H), 6.49(d, J=9.0 Hz, 1H), 3.87(t, J=6.0 HZ, 1H), 3.68-3.58(m, 4H), 2.91(t, J=7.5 Hz, 2H), 1.89-1.78(m, 2H), 1.71-1.61(m, 2H), 1.50-1.41(m, 2H); $^{13}$C-NMR (300 MHz CD$_3$OD) δ: 170.7, 146.5, 145.8, 145.3, 138.4, 123.3, 100.3, 54.3, 52.1, 40.3, 39.0, 32.0, 28.0, 23.0; Abs$_{max}$/Em$_{max}$(PBS): 475 nm/539 nm; [α]$^{23}_D$=+21.1 cm$^3$·g$^{-1}$·dm$^{-1}$ (c=1.0 g cm$^{-3}$ in MeOH); Elemental Anal. calcd (%) for C$_{14}$H$_{23}$Cl$_2$N$_7$O$_4$.1/2H$_2$O.1/2CH$_3$OH: C, 38.76; H, 5.83; N, 21.82. found: C, 38.46; H, 5.50; N, 21.59; MALDI-TOFMS m/z: 352 [M+H]$^+$.

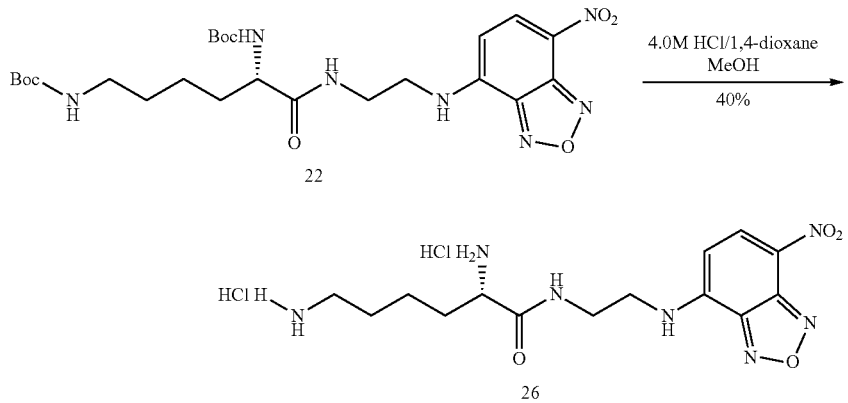

24) Synthesis of a Target Compound 27 (Compound A) (Kε3-NBD)

Under an Ar atmosphere, intermediate 23 (71.5 mg, 0.071 mmol) was dissolved in anhydrous methanol (1 mL) and a 4.0 N solution of hydrochloric acid in 1,4-dioxane (1 mL), and the solution was shaded from the light and stirred for 5.5 hours. After confirming completion of the reaction by TLC (methylene chloride:methanol=9:1), the reaction solution was air-dried. After evaporation under a reduced pressure, the material was recrystallized from methanol/ethyl acetate, to give a target compound 27 (compound A) (Kε3-NBD) (46.3 mg, 87%) as an orange solid.

Mp 183.3-184.7° C.; $^1$H-NMR (300 MHz, CD$_3$OD) δ: 8.56(d, 1H, J=9.0 Hz), 6.51(d, 1H, J=9.0 Hz), 3.94-3.77(m, 6H), 3.54-3.49(m, 2H), 3.24-3.10(m, 3H), 2.97(t, 2H, J=7.75 Hz), 1.96-1.81(m, 5H), 1.76-1.68(m, 4H), 1.65-1.60(m, 2H), 1.55-1.38(m, 9H). MALDI-TOF/MS; 608.319 [M+H] (compound 27: $C_{26}H_{45}N_{11}O_6$=607.36)

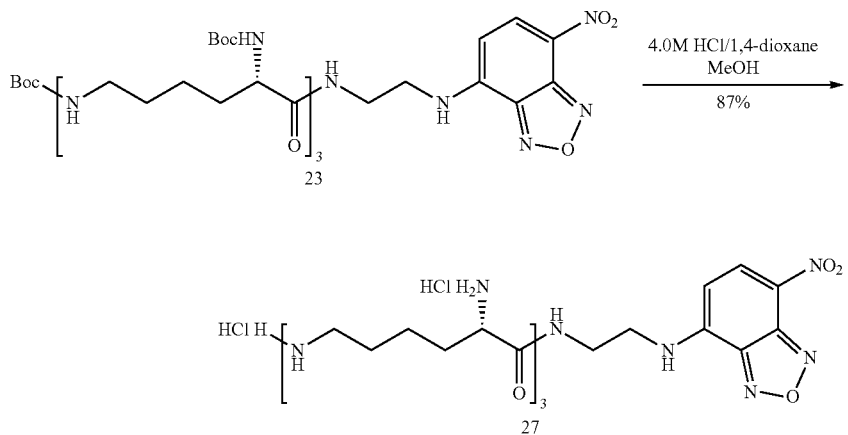

25) Synthesis of a Target Compound 28 (Kε4-NBD)

Under an Ar atmosphere, intermediate 24 (102.8 mg, 0.083 mmol) was dissolved in anhydrous methanol (2 mL) and a 4.0 N solution of hydrochloric acid in 1,4-dioxane (2 mL), and the solution was shaded from the light and stirred for 2 hours. After confirming completion of the reaction by TLC (methylene chloride:methanol=9:1), the reaction solution was air-dried. After evaporation under a reduced pressure, the material was recrystallized from methanol/ethyl acetate to give a target compound 28 (Kε4-NBD) (66.2 mg, 87%) as an orange solid.

$^1$H-NMR (300 MHz, CD$_3$OD) δ: 8.56(d, J=9.0 Hz, 1H), 6.50(d, J=9.0 Hz, 1H), 3.87-3.78(m, 7H), 3.55-3.52(m, 1H), 3.21-3.10(m, 5H), 2.96(t, J=7.5 Hz, 2H), 1.94-1.37(m, 26H); Abs$_{max}$/Em$_{max}$(PBS): 476 nm/540 nm; Anal. calcd for $C_{32}H_{62}Cl_5N_{13}O_7 \cdot 3H_2O$: C, 39.53; H, 7.05; N, 18.73. found: C, 39.57; H, 6.82; N, 18.58.

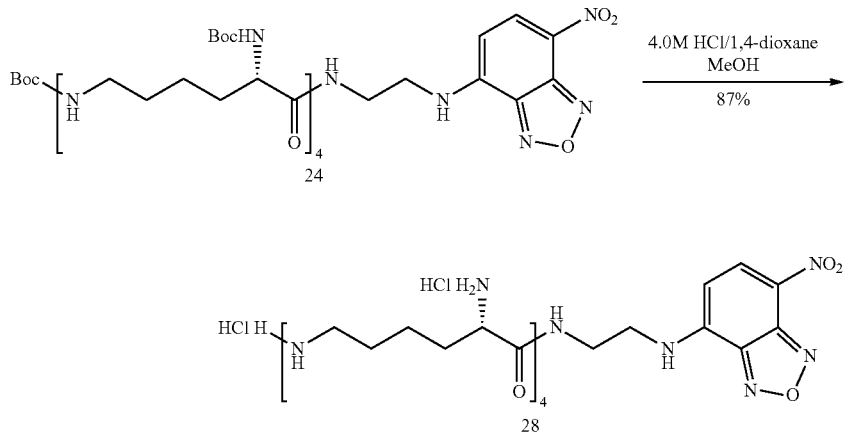

26) Synthesis of a Target Compound 29 (Kε5-NBD)

Under an Ar atmosphere, intermediate 25 (76.4 mg, 0.052 mmol) was dissolved in anhydrous methanol (2 mL) and a 4.0 N solution of hydrochloric acid in 1,4-dioxane (2 mL), and the solution was shaded from the light and stirred for 1 hour. After confirming completion of the reaction by TLC (methylene chloride:methanol=9:1), the reaction solution was air-dried. After evaporation under a reduced pressure, the material was recrystallized from methanol/ethyl acetate, to give a target compound 29 (Kε5-NBD) (41.4 mg, 73%) as an orange solid.

$^1$H-NMR (300 MHz, CD$_3$OD) δ: 8.56(d, J=9.0 Hz, 1H), 6.51(d, J=9.0 Hz, 1H), 4.00-3.68(m, 8H), 3.57-3.48(m, 1H), 3.34-3.07(m, 7H), 2.97(t, J=7.5 Hz, 2H), 1.92-1.82(m, 8H), 1.79-1.68(m, 4H), 1.61(t, J=6.5 Hz, 7H), 1.46(br s, 12H); Abs$_{max}$/Em$_{max}$(PBS): 476 nm/539 nm; Anal. calcd for C$_{38}$H$_{69}$N$_{15}$O$_8$.4H$_2$O.CH$_3$OH: C, 39.46; H, 7.39; N, 17.70. found: C, 39.44; H, 7.00; N, 17.55.

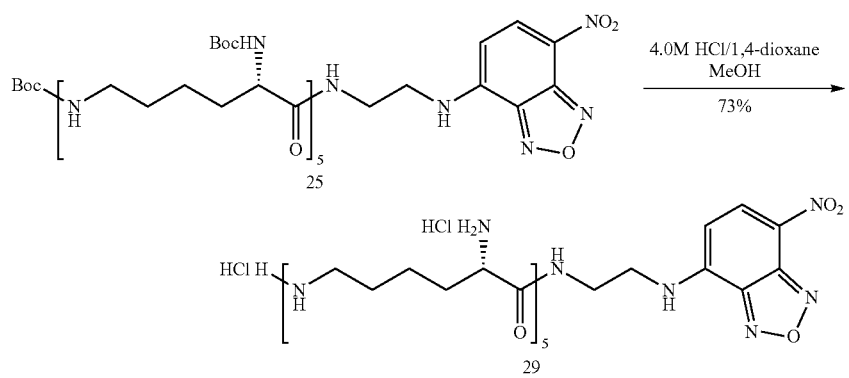

27) Synthesis of Intermediate 31

To anhydrous methanol (60 mL) were added activated molecular sieves 4A, ethyl 4-aminobenzoate (30) (1.7 g, 10 mmol), acetic acid (0.63 mL, 11 mmol) and N-tert-butoxycarbonyl-2-aminoacetaldehyde (1.9 g, 12 mmol), and the mixture was stirred under an Ar atmosphere at room temperature for 29 hours. After confirming completion of the reaction by TLC (ethyl acetate:n-hexane:methylene chloride=1:2:3), sodium cyanoborohydride (0.6 g, 10 mmol), and the mixture was stirred at room temperature for 14 hours. After confirming completion of the reaction by TLC (ethyl acetate:n-hexane:methylene chloride=1:2:3), water (10 mL) was added to the reaction solution, which was then filtered through a Celite pad with ethyl acetate. The filtrate was washed with a 2N aqueous hydrochloric acid solution (50 mL), a saturated aqueous sodium hydrogen carbonate solution (100 mL) and saturated saline (100 mL), and dried over anhydrous magnesium sulfate. After evaporation under a reduced pressure, the obtained material was purified by flash column chromatography (ethyl acetate:n-hexane:methylene chloride=1:5:4), to give intermediate 31 (2.38 g, 77%) as a white solid.

$^1$H-NMR (300 MHz, CDCl$_3$) δ: 7.88(d, 2H, J=9.0 Hz), 6.56(d, 2H, J=9.0 Hz), 4.81(s, 1H), 4.68(s, 1H), 4.32(q, 2H, J=7.0 Hz), 3.40(t, 2H, J=6.0 Hz), 3.31(br s, 2H), 1.46(s, 9H), 1.36(t, 3H, J=7.0 Hz).

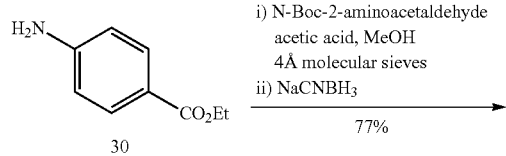

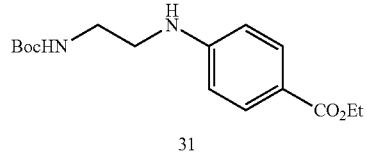

28) Synthesis of Intermediate 32

Intermediate 31 (806 mg, 2.6 mmol), iodine (1.32 g, 5.2 mmol), silver sulfate (1.78 g, 5.7 mmol) were dissolved in anhydrous methanol (10 mL), and the mixture was shaded from the light and stirred under an Ar atmosphere at room temperature for 1.5 hours. After confirming completion of the reaction by TLC (ethyl acetate:n-hexane=1:3), an excessive amount of a saturated aqueous sodium thiosulfate solution was added to the reaction solution, which was filtered through a Celite pad with ethyl acetate. The filtrate was poured into water (50 mL). The mixture was extracted with ethyl acetate (3×50 mL), and the organic layer was washed with water (50 mL) and saturated saline (50 mL) and then dried over anhydrous magnesium sulfate. After evaporation under a reduced pressure, the obtained material was purified by flash column chromatography (ethyl acetate:n-hexane=1:7), to give intermediate 32 (1.14 g, 78%) as a white solid.

$^1$H-NMR (300 MHz, CDCl$_3$) δ: 8.41(s, 2H), 4.84(br s, 1H), 4.35(q, 2H, J=7.1 Hz), 4.07(br s, 1H), 3.41(br s, 4H), 1.45(s, 9H), 1.38(t, 3H, J=7.1 Hz).

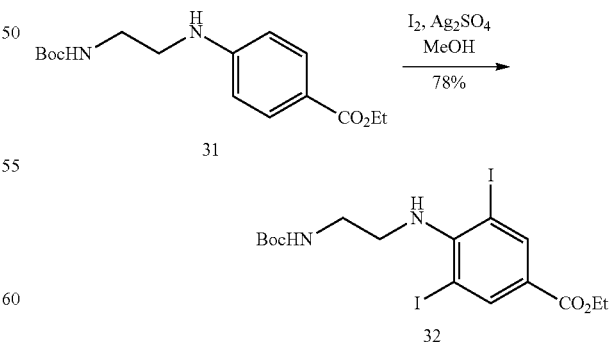

29) Synthesis of Intermediate 33

Intermediate 32 (562 mg, 1.0 mmol) was dissolved in anhydrous methylene chloride (5 mL). After adding trifluoroacetic acid (2 mL), the solution was shaded from the light and stirred at room temperature for 1.5 hours. After confirming completion of the reaction by TLC (ethyl acetate:n-hexane=1:1), the reaction solution was poured into water (10 mL). After adding a saturated aqueous sodium hydrogen carbonate solution (50 mL), the mixture was extracted with ethyl acetate (3×50 mL), and the organic layer was washed with water (50 mL) and saturated saline (50 mL) and then dried over anhydrous magnesium sulfate. After evaporation under a reduced pressure, yellow and viscous intermediate 33 (364 mg, 79%) was obtained.

$^1$H-NMR (300 MHz, CDCl$_3$) δ: 8.41(s, 2H), 4.35(q, 2H, J=7.1 Hz), 3.40(br s, 2H), 3.04(br s, 2H), 2.05(br s, 2H), 1.38(t, 3H, J=7.1 Hz).

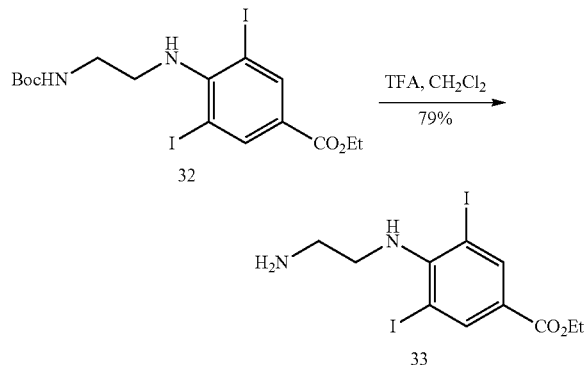

30) Synthesis of Intermediate 34

Intermediate 32 (560 mg, 1.0 mmol) was dissolved in THF (3.0 mL) and water (1.0 mL). After adding lithium hydroxide monohydrate (62.9 mg, 1.5 mmol), the mixture was stirred at 40° C. for 13 hours. After confirming completion of the reaction by TLC (ethyl acetate:n-hexane=1:3), 0.1N aqueous hydrochloric acid solution (20 mL) was added to the reaction solution, and the precipitated solid was collected by filtration and washed with water to give intermediate 34 (498 mg, 94%) as a white solid.

$^1$H-NMR (300 MHz, CD$_3$OD) δ: 8.38(s, 2H), 6.72(br s, 1H), 3.41(t, 2H, J=6.0 Hz), 1.43(s, 9H).

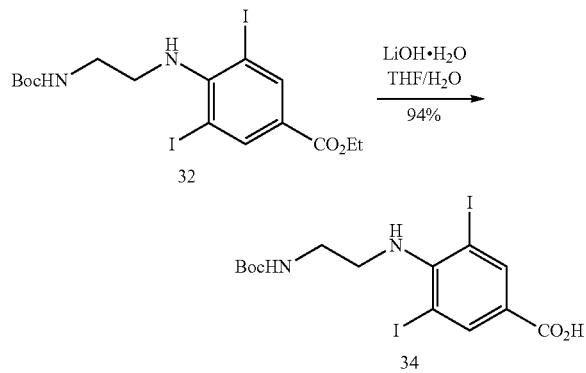

31) Synthesis of Intermediate 36

Guanidine hydrochloride (35) (1.45 g, 15 mmol) was dissolved in anhydrous 1,4-dioxane (25 mL). Under ice-cooling, a 4.5N aqueous sodium hydroxide solution (12.5 mL) and di-tert-butyl dicarbonate (7.2 mL, 32 mmol) were sequentially added dropwise, and the mixture was stirred for 24 hours. After confirming completion of the reaction by TLC (ethyl acetate:n-hexane=1:4), the reaction solution was poured into water (50 mL). The mixture was extracted with ethyl acetate (3×70 mL), and the organic layer was washed with water (2×50 mL) and saturated saline (2×50 mL) and then dried over anhydrous magnesium sulfate. After evaporation under a reduced pressure, the obtained material was purified by flash column chromatography (ethyl acetate:n-hexane:methylene chloride=1:6:1), to give intermediate 36 (1.93 g, 49%) as a white solid.

$^1$H-NMR (300 MHz, DMSO-d6) δ: 10.45(br s, 1H), 8.48(br s, 2H), 1.40(s, 18H).

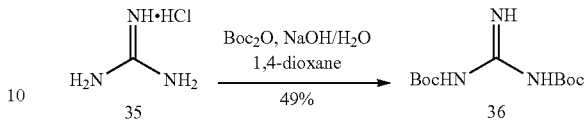

32) Synthesis of Intermediate 37

Under an Ar atmosphere, intermediate 36 (1.93 g, 7.4 mmol) and triethylamine (2.1 mL, 14.8 mmol) were dissolved in anhydrous methylene chloride (15 mL). The solution was cooled to −78° C., followed by trifluoromethanesulfonic anhydride (1.9 mL, 11.6 mmol) dropwise over 10 min. The mixture was stirred at room temperature for 20 hours. After confirming completion of the reaction by TLC (ethyl acetate:n-hexane=1:4), the reaction solution was poured into a saturated aqueous ammonium chloride solution (100 mL). The mixture was extracted with methylene chloride (3×50 mL), and the organic layer was washed with water (100 mL) and saturated saline (100 mL) and then dried over anhydrous magnesium sulfate. After evaporation under a reduced pressure, the obtained material was purified by flash column chromatography (ethyl acetate:n-hexane=1:10), to give intermediate 37 (786 mg, 27%) as a white solid.

$^1$H-NMR (300 MHz, DMSO-d6) δ: 11.09(br s, 2H), 1.45(s, 18H).

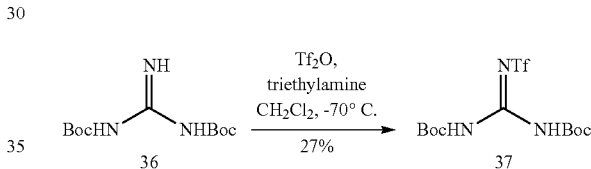

33) Synthesis of Intermediate 38

Under an Ar atmosphere, intermediate 37 (364 mg, 0.8 mmol) and intermediate 33 (318 mg, 0.8 mmol) were dissolved in anhydrous methylene chloride (5 mL). Triethylamine (0.44 mL, 3.2 mmol) was added and the solution was stirred at room temperature for 16.5 hours. After confirming completion of the reaction by TLC (ethyl acetate:n-hexane=1:2), the reaction solution was poured into a saturated aqueous ammonium chloride solution (20 mL). The mixture was extracted with ethyl acetate (3×30 mL), and the organic layer was washed with water (50 mL) and saturated saline (50 mL) and then dried over anhydrous magnesium sulfate. After evaporation under a reduced pressure, the obtained material was purified by flash column chromatography (ethyl acetate:n-hexane:methylene chloride=2:75:50), to give intermediate 38 (524 mg, 94%) as a white foamy solid.

$^1$H-NMR (300 MHz, CDCl$_3$) δ: 11.49(s, 1H), 8.63(br s, 1H), 8.41(s, 2H), 4.34(q, 2H, J=7.25 Hz), 3.72(q, 2H, J=5.75 Hz), 3.54(q, 2H, J=5.75 Hz), 1.51(s, 9H), 1.49(s, 9H), 1.38(t, 3H, J=7.25 Hz).

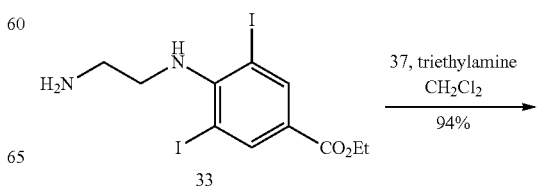

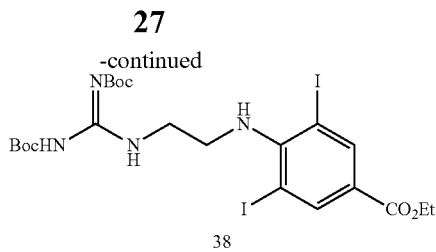

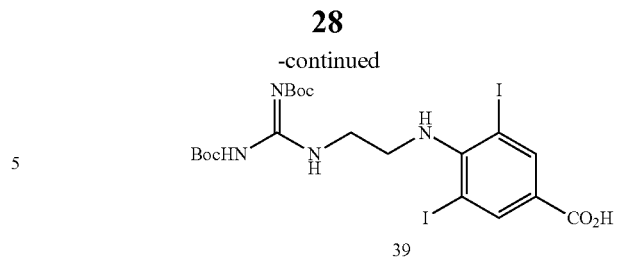

34) Synthesis of Intermediate 39

Intermediate 38 (518 mg, 0.7 mmol) was dissolved in THF (6.0 mL) and water (2.0 mL). Lithium hydroxide monohydrate (111 mg, 2.6 mmol) was added and the mixture was stirred at 40° C. for 23 hours. After confirming completion of the reaction by TLC (ethyl acetate:n-hexane=1:2), the reaction solution was poured into 0.1N aqueous hydrochloric acid solution (20 mL). The mixture was extracted with ethyl acetate (3×50 mL), and the organic layer was washed with water (50 mL) and saturated saline (50 mL) and then dried over anhydrous magnesium sulfate. After evaporation under a reduced pressure, intermediate 39 (503 mg, q.y.) was obtained as a white foamy solid.

$^1$H-NMR (300 MHz, CDCl$_3$) δ: 11.49(br s, 1H), 8.62(br s, 1H), 8.45(s, 2H), 3.72(q, 2H, J=5.75 Hz), 3.60(t, 2H, J=5.75 Hz), 1.51(s, 9H), 1.49(s, 9H). FAB-MS m/e:675[M+H]$^+$

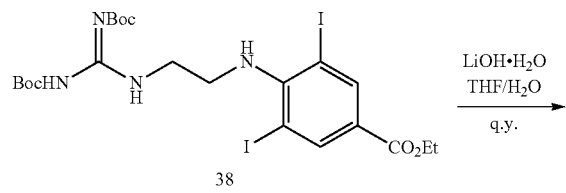

35) Synthesis of Intermediate 40

Under an Ar atmosphere and shading from the light, compound 27 (compound A) (17.4 mg, 0.023 mmol) and intermediate 39 (74.5 mg, 0.110 mmol) were dissolved in anhydrous DMF (3 mL), followed by addition of triethylamine (29 μL, 0.207 mmol). Under ice-cooling, HOBt.H$_2$O (18.3 mg, 0.119 mmol) and EDCI.HCl (22.3 mg, 0.116 mmol) were sequentially added, and the mixture was allowed to be warmed to room temperature and stirred for 27.5 hours. After confirming completion of the reaction by TLC (ethyl acetate:methylene chloride=9:1), the reaction solution was poured into water (20 mL). The mixture was extracted with methylene chloride (3×30 mL), and the organic layer was washed with saturated saline (50 mL) and then dried over anhydrous magnesium sulfate. After evaporation under a reduced pressure, the obtained material was purified by flash column chromatography (methylene chloride:methanol=9:1), to give brown and viscous intermediate 40 (16.3 mg, 22%).

$^1$H-NMR (300 MHz, CDCl$_3$) δ: 11.50(s, 4H), 8.46(d, 1H, J=9.0 Hz), 8.26(s, 2H), 8.21(s, 4H), 8.15(s, 2H), 6.11(d, 1H, J=9.0 Hz), 4.53(br s, 3H), 3.99(br s, 3H), 3.67-3.63(m, 7H), 3.44(br s, 10H), 1.49(s, 80H).

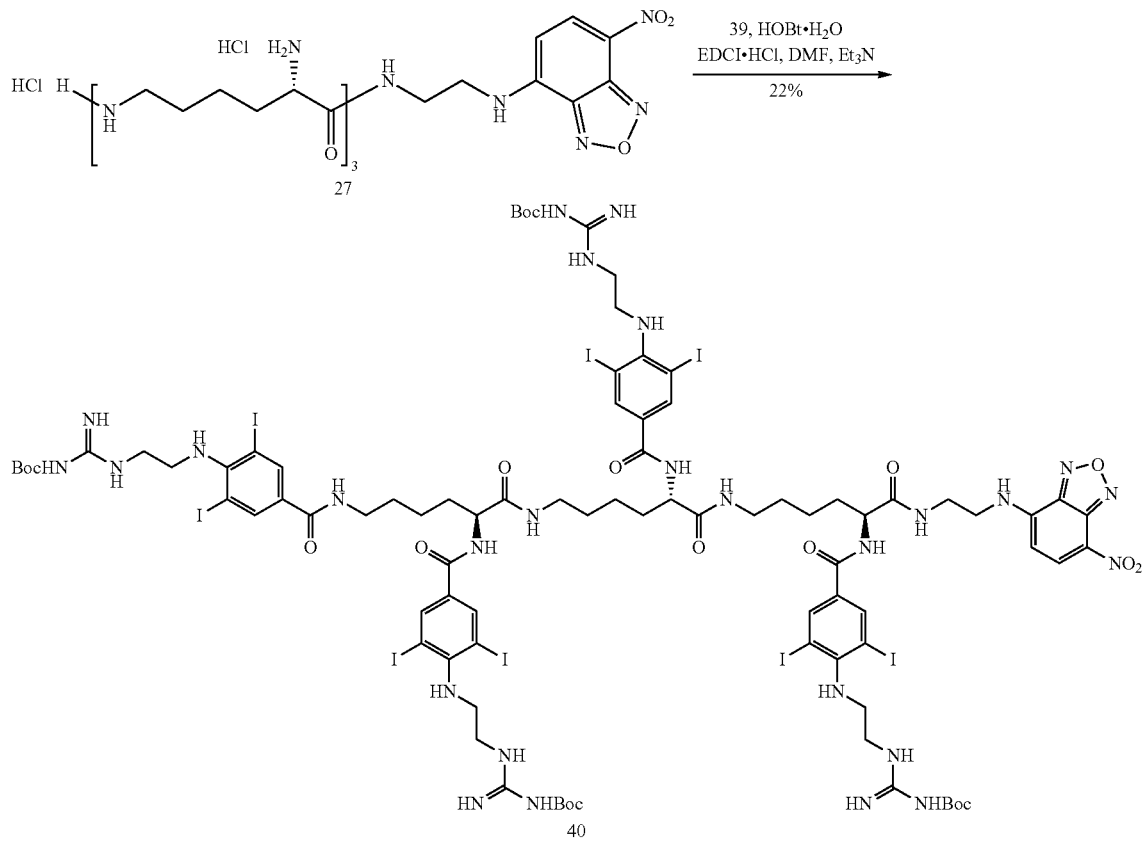

36) Synthesis of Intermediate 41

Under an Ar atmosphere and shading from the light, compound 27 (compound A) (13.0 mg, 0.017 mmol) and intermediate 34 (51.0 mg, 0.096 mmol) were dissolved in anhydrous DMF (3 mL), followed by adding triethylamine (21 μL, 0.153 mmol). Under ice-cooling, 1-hydroxybenzotriazole monohydrate (13.5 mg, 0.088 mmol) and 1-(3-dimethylaminopropyl)-3-ethylcarbodiimide hydrochloride (16.3 mg, 0.085 mmol) were sequentially added, and the mixture was stirred for 20 hours. After confirming completion of the reaction by TLC (methylene chloride:methanol=9:1), the reaction solution was poured into a saturated aqueous sodium hydrogen carbonate solution (30 mL) and the mixture was extracted with ethyl acetate (3×30 mL). The organic layer was washed with a saturated aqueous ammonium chloride solution (50 mL) and saturated saline (50 mL) and then dried over anhydrous magnesium sulfate. After evaporation under a reduced pressure, the obtained material was purified by flash column chromatography (methylene chloride:n-hexane:ethyl acetate:methanol=9:5:4:1), to give intermediate 41 (74.8 mg, 81%) as an orange foamy solid.

$^1$H-NMR (300 MHz, CD$_3$OD) δ: 8.42(d, 1H, J=9.0 Hz), 8.42-8.20(m, 8H), 8.16(br s, 1H), 8.10(br s, 1H), 6.71(br s, 3H), 6.33(d, 1H, J=9.0 Hz), 4.43-4.35(m, 3H), 3.63(br s, 3H), 3.56-3.53(m, 3H), 1.78(br s, 6H), 1.43(s, 36H).

37) Synthesis of a Target Compound 42 (Compound B)

Under an Ar atmosphere, intermediate 40 (15.7 mg, 4.1 μmol) was dissolved in anhydrous methanol (0.5 mL), anhydrous methylene chloride (0.5 mL) and a 4.0N hydrochloric acid in 1,4-dioxane (1.0 mL), and the solution was stirred for 11.5 hours under shading from the light. After confirming completion of the reaction by TLC (methylene chloride:methanol=9:1), the reaction solution was air-dried. After evaporation under a reduced pressure, the obtained material was recrystallized from methanol/ethyl acetate to give a target compound 42 (compound B) (4.2 mg, 40%) as an orange solid.

Mp 189.4-191.5° C.; $^1$H-NMR (300 MHz, CD$_3$OD) δ: 8.53-8.47(m, 6H), 8.36-8.31(m, 7H), 8.25-8.13(m, 10H), 6.33(d, 1H, J=9.0 Hz), 4.36(br s, 3H), 3.66-3.62(m, 4H), 3.48-3.40(m, 25H), 1.85-1.76(m, 9H), 1.65-1.43(m, 21H); MALDI-TOF/MS m/e: 2431.913[M+H] (compound 42: $C_{66}H_{85}I_8N_{27}O_{10}$=2430.93)

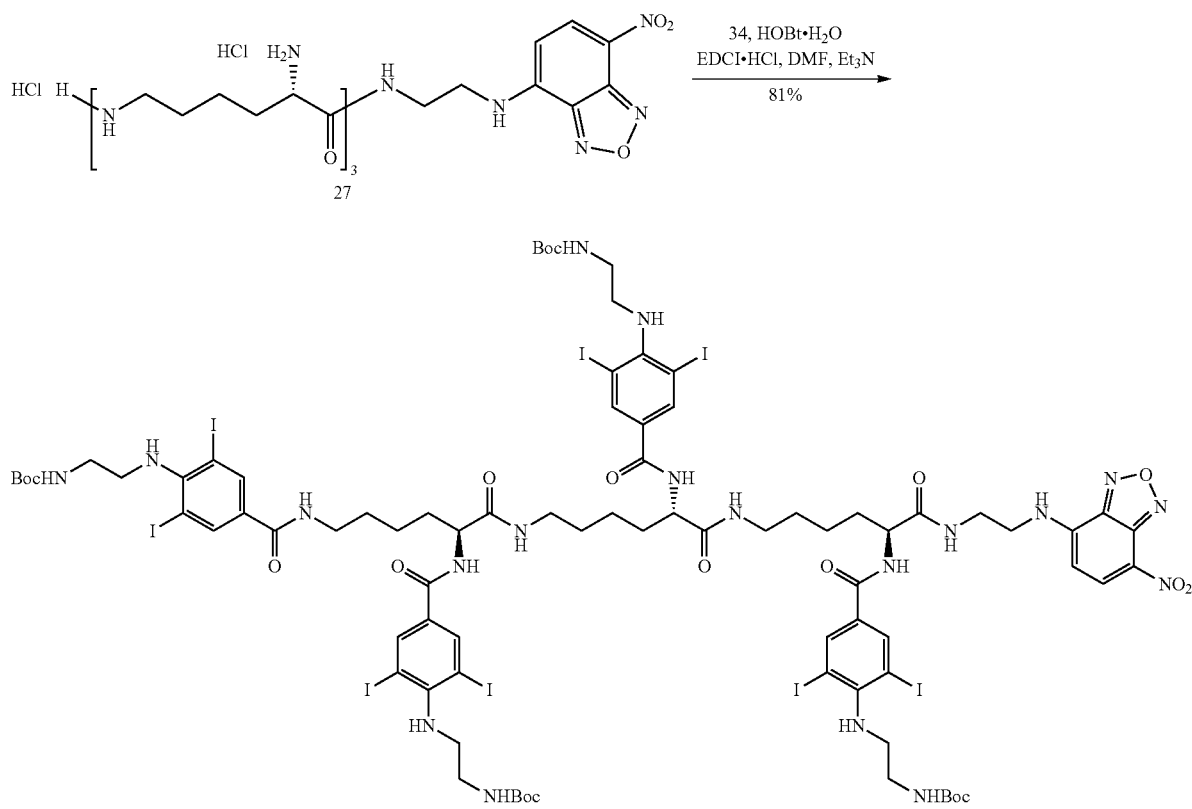

41

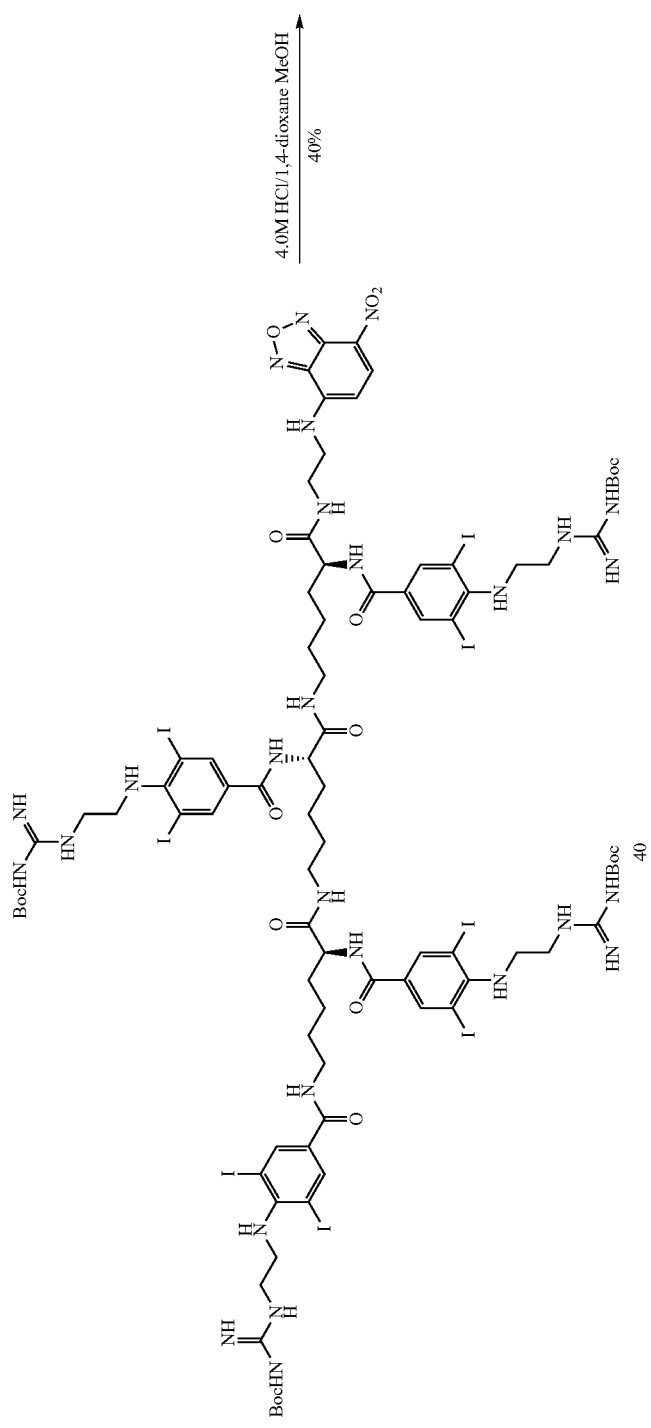

-continued
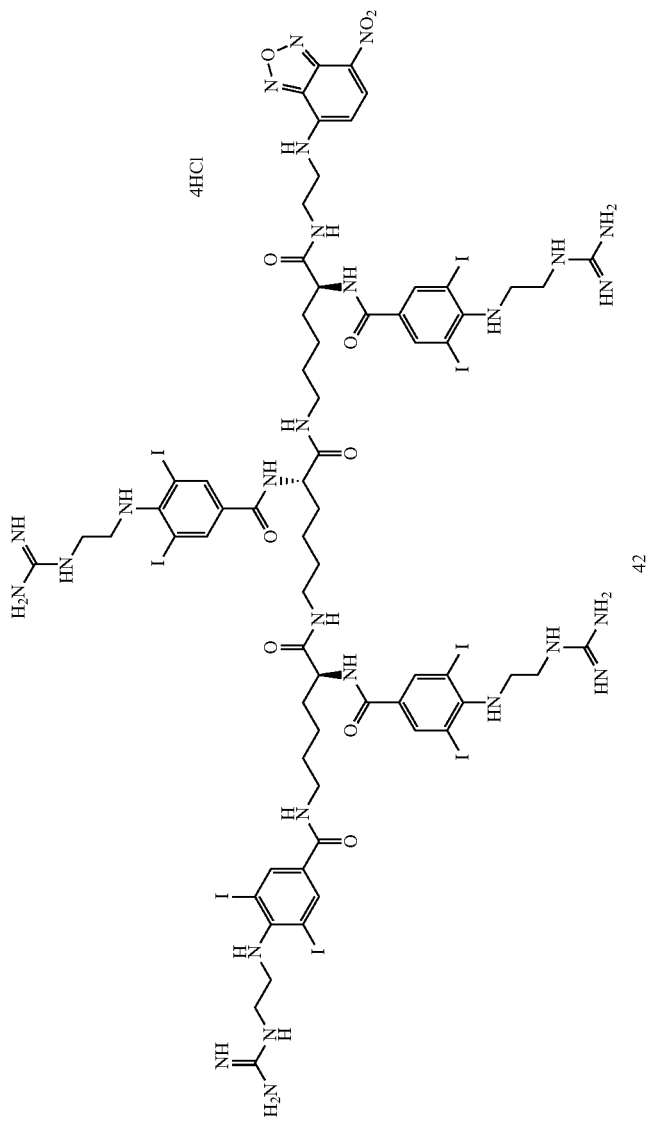
42

38) Synthesis of Compound 43 (Compound C)

Under an Ar atmosphere, intermediate 41 (3.9 mg, 1.5 μmol) was dissolved in anhydrous methanol (0.5 mL) and a 4.0 N solution of hydrochloric acid in 1,4-dioxane (0.5 mL), and the solution was stirred for 10.5 hours under shading from the light. After confirming completion of the reaction by TLC (methylene chloride:methanol=19:1), the reaction solution was air-dried. After evaporation under a reduced pressure, the obtained material as recrystallized from methanol/ethyl acetate, to give compound 43 (compound C) (2.5 mg, 69%) as an orange solid.

Mp 192.9-195.7° C.; $^1$H-NMR (300 MHz, CD$_3$OD) δ: 8.43-8.23(m, 9H), 6.33(d, 1H, J=9.0 Hz), 4.38(br s, 4H), 3.66(br s, 7H), 1.79(br s, 8H), 1.49(br s, 18H); MALDI-TOF/MS; 2301.939 [M+HCl+H] (compound 43: $C_{62}H_{77}I_8N_{19}O_{10}$=2262.85)

aminoethane (32 μL, 0.2 mmol) were dissolved in anhydrous DMF (3 mL). Under ice-cooling, 1-hydroxybenzotriazole monohydrate (37 mg, 0.24 mmol) and 1-(3-dimethylaminopropyl)-3-ethylcarbodiimide hydrochloride (46 mg, 0.24 mmol) were sequentially added, and the mixture was stirred at room temperature for 13.5 hours. After confirming completion of the reaction by TLC (n-hexane:ethyl acetate=1:1), the reaction solution was poured into water (30 mL). The mixture was extracted with ethyl acetate (3×30 mL), and the organic layer was washed with a saturated aqueous sodium hydrogen carbonate solution (50 mL) and saturated saline (50 mL) and then dried over anhydrous magnesium sulfate. After evaporation under a reduced pressure, the obtained material was recrystallized from n-hexane/ethyl acetate, to give intermediate 45 (106 mg, 82%) as a white solid.

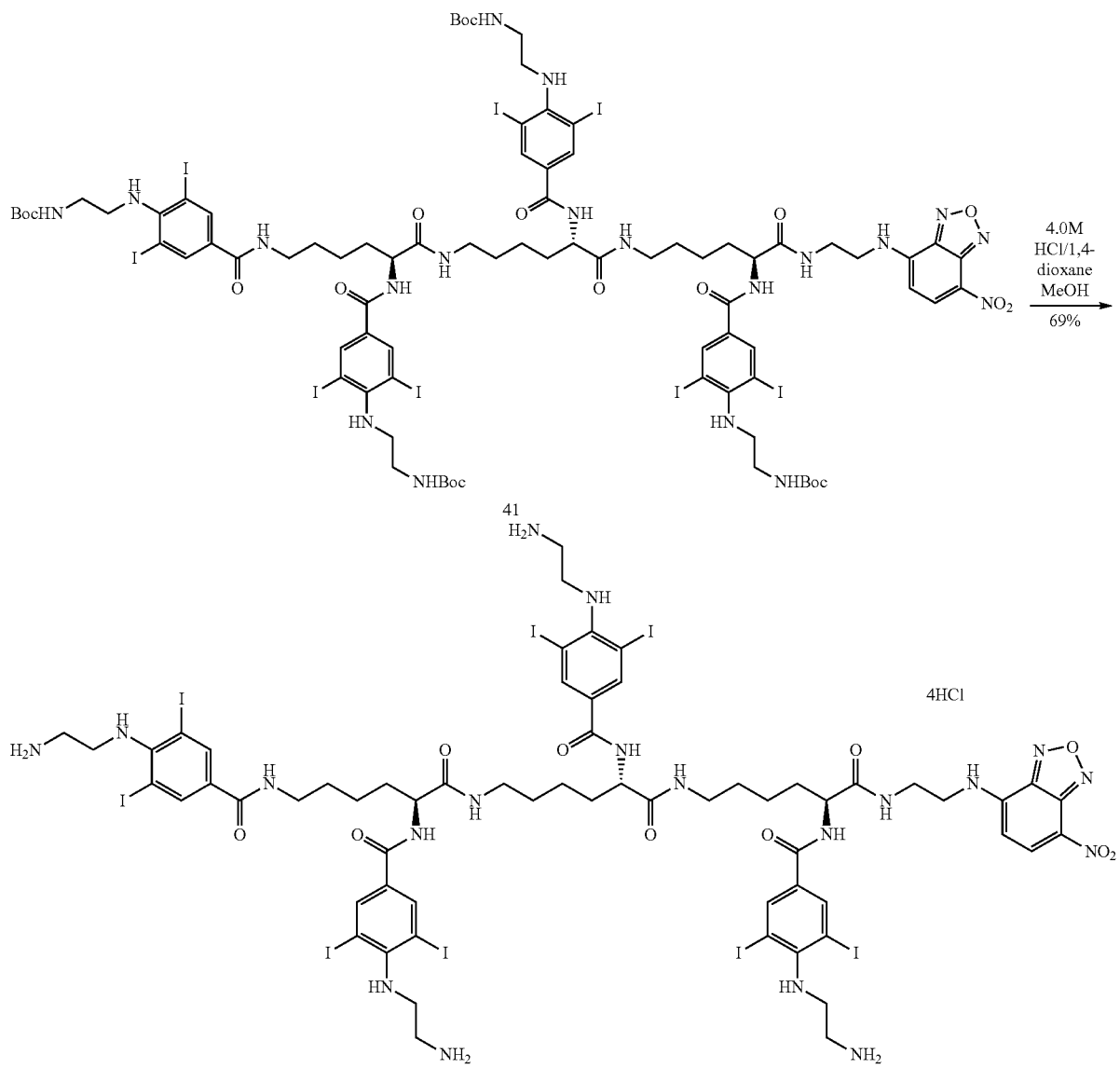

39) Synthesis of Intermediate 45

Under an Ar atmosphere, 2,3,5-triiodobenzoic acid (44) (100 mg, 0.2 mmol) and N-(tert-butoxycarbonyl)-1,2-di- $^1$H-NMR (300 MHz, CDCl$_3$) δ: 8.22(d, J=2.0 Hz, 7.53(d, J=2.0 Hz, 1H), 6.50(br s, 1H), 4.91(br s, 1H), 3.53(q, J=5.4 Hz, 2H), 3.40(br s, 2H), 1.44(s, 9H).

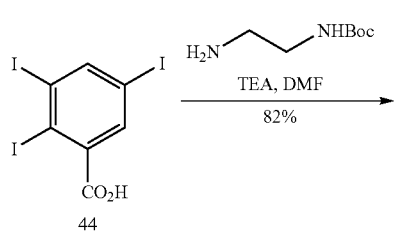

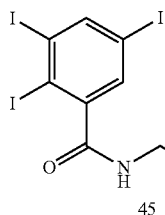

40) Synthesis of Intermediate 46

Under an Ar atmosphere, intermediate 45 (415 mg, 0.65 mmol) was dissolved in anhydrous methanol (10 mL) and a 4.0 N solution of hydrochloric acid in 1,4-dioxane (6 mL), and the mixture was stirred for 2 hours. After confirming completion of the reaction by TLC (n-hexane:ethyl acetate=1:1), the reaction solution was air-dried. After evaporation under a reduced pressure, the obtained material was recrystallized from methanol/ethyl acetate, to give intermediate 46 (326.2 mg, 87%) as a white solid.

$^1$H-NMR (300 MHz, CD$_3$OD) δ: 8.34(d, J=2.0 Hz, 1H), 7.71(d, J=2.0 Hz, 1H), 3.60(t, J=6.5 Hz, 2H), 3.17(t, J=6.5 Hz, 2H); MALDI-TOFMS m/z: 543 [M+H]$^+$.

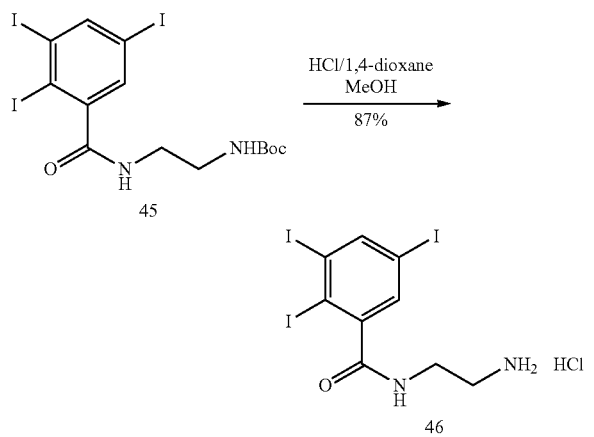

41) Synthesis of Intermediate 47

Under an Ar atmosphere, intermediate 18 (289 mg, 0.23 mmol) and intermediate 46 (133 mg, 0.23 mmol) were dissolved in anhydrous DMF (8 mL). Under ice-cooling, 1-hydroxybenzotriazole monohydrate (43 mg, 0.28 mmol) and 1-(3-dimethylaminopropyl)-3-ethylcarbodiimide hydrochloride (54 mg, 0.28 mmol) were sequentially added, and the mixture was allowed to be warmed to room temperature, and then stirred for 2 hours. After confirming completion of the reaction by TLC (methylene chloride:methanol=9:1), the reaction solution was poured into water (70 mL) and the mixture was extracted with ethyl acetate (3×70 mL). The organic layer was washed with water (50 mL) and saturated saline (50 mL) and then dried over anhydrous magnesium sulfate. After evaporation under a reduced pressure, the obtained material was purified by flash column chromatography (methylene chloride:methanol=19:1), to give intermediate 47 (158 mg, 39%) as a white solid.

$^1$H-NMR (300 MHz, CDCl$_3$) δ: 8.30(d, J=2.0 Hz, 1H), 7.63(d, J=7.0 Hz, 1H), 3.94(br s, 5H), 3.44(br s, 3H), 3.20-3.07(m, 10H), 3.02(d, J=6.5 Hz, 2H), 0.71(br s, 5H), 1.51(d, J=6.5 Hz, 21H), 1.44-1.42(m, 54H).

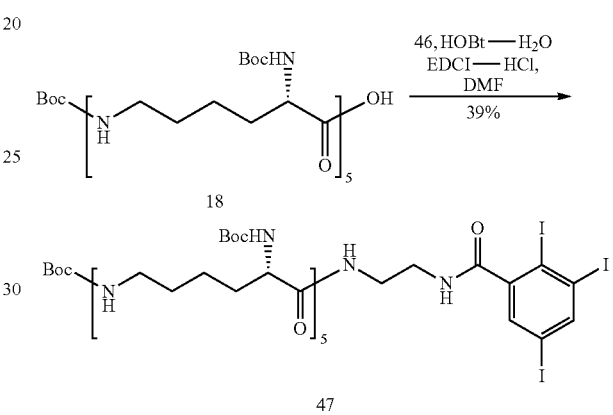

42) Synthesis of a Compound 48 (Compound D) (Kε5-TIB)

Under an Ar atmosphere, intermediate 47 (100 mg, 0.056 mmol) was dissolved in anhydrous methanol (2 mL) and a 4.0 N solution of hydrochloric acid in 1,4-dioxane (1 mL), and the solution was stirred for 1 hour. After confirming completion of the reaction by TLC (methylene chloride:methanol=9:1), the reaction solution was air-dried. After evaporation under a reduced pressure, the obtained material was recrystallized from methanol/ethyl acetate, to give target compound 48 (compound D) (74 mg, 95%) as a white solid.

m.p. 208.0-209.5° C.; $^1$H-NMR (300 MHz, CD$_3$OD) δ: 8.32(d, J=2.0 Hz, 1H), 7.66(d, J=2.0 Hz, 1H), 3.96-3.85(m, 5H), 3.59-3.47(m, 1H), 3.24(br s, 6H), 2.97(t, J=7.5 Hz, 2H), 1.87(br s, 10H), 1.74(br s, 2H), 1.60(d, J=6.5 Hz, 9H), 1.48(br s, 11H); $^{13}$C-NMR (300 MHz, CD$_3$OD) δ: 171.5, 170.6, 170.2, 170.1, 148.7, 147.9, 136.3, 113.2, 107.7, 97.2, 95.0, 61.6, 54.5, 54.3, 50.0, 40.4, 40.1, 32.3, 32.2, 29.8, 28.0, 23.4, 23.1, 20.9, 14.5; [α]$^{21}$D =+19.9 cm$^3$ g$^{-1}$ dm$^{-1}$ (c=1.0 g cm$^{-3}$ in MeOH); Elemental Anal. calcd (%) for C$_{39}$H$_{75}$Cl$_{613}$N$_{12}$O$_6$.3/2H$_2$O: C, 32.79; H, 5.50; N, 11.77; found: C, 33.01; H, 5.52; N, 11.41. MALDI-TOFMS m/z: 1183 [M+H]$^+$.

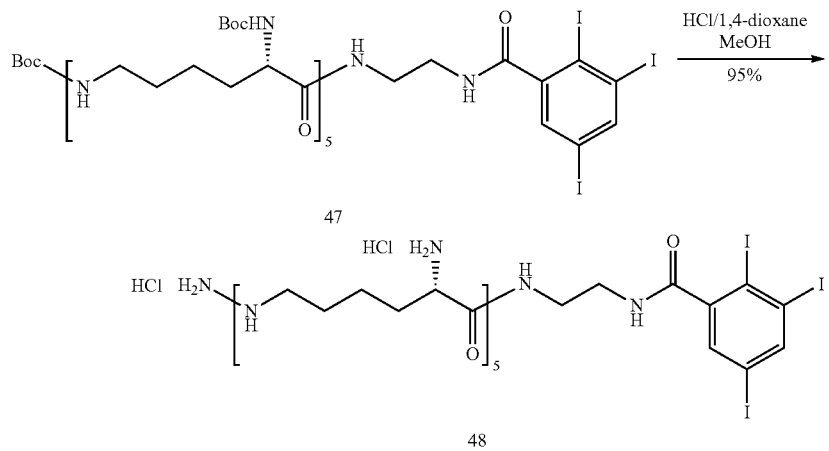

47

48

[Immersion of a Distal End of a Femur of a Normal Mouse in a Solution of a Cartilage Tissue Visualization Reagent and Ex Vivo Detection]

Two normal C57B6/J strain mouse (8 week old, female) were prepared. The animals were euthanized by ether deep anesthesia and a distal end of a femur was excised. The sample was immersed in 100 μL of a 0.1 mM lysine oligomer derivative solution at room temperature for 1 hour. After 1 hour, the sample was washed twice with buffered saline. This was embedded in 4% CMC compound, frozen in hexane/liquid nitrogen, and cut into thin slices with a thickness of 7 μm using a tungsten carbide blade TC-65 (Leica) for a hard tissue slice and Cryofilm (Leica) in a cryostat without decalcification. The slice was thawed at room temperature for 10 sec, immersed in 100% ethanol for about 30 sec, stored in 4% paraformaldehyde (PFA) for a while, washed with tap water, and then subjected to fluorescence microscopy. An optical filer was a GFP filter. A lysine peptide was labeled with a fluorescence agent NBD, so that its signal was detected.

FIG. 1 shows staining images of a cartilage when three compounds A to C below were used as a lysine oligomer derivative. Here, a solvent of the solution of a lysine oligomer derivative was saline containing 25% ethanol. FIG. 1 is an enlarged image of an articular cartilage area in a sagittal plane of a knee joint in a distal end of a femur. The broken line indicates a tide-mark which is a boundary plane between a cartilage and a calcified cartilage layer. Fluorescence signals (green in a color photo) were observed from the surface layer of the cartilage layer to the tide-mark, indicating that the lysine oligomer derivative was not bonded to the calcified cartilage layer. Staining was observed in the cartilage tissue for Compounds A and B, while staining was confined to the surface tissue for Compound C.

A: compound 27
B: compound 42
C: compound 43

FIG. 2 shows staining images of a cartilage when four compounds below were used as a lysine oligomer derivative. Here, a solvent of the solution of a lysine oligomer derivative was saline. FIG. 2 is an enlarged image of an articular cartilage area in a sagittal plane of a knee joint in a distal end of a femur. A fluorescence signal was observed from the surface layer of the cartilage layer to the tide-mark, indicating that the lysine oligomer derivative did not penetrate into the calcified cartilage layer. For any of compounds 26 to 29, staining of a cartilage tissue was observed. However, staining of compound 26 containing only one lysine unit was slight. On the other hand, it was observed that compound 27 containing three lysine units was adequately stained and compounds 28 and 29 containing 4 or 5 lysine units was further strongly stained. The white (green in a color photo) regions in the cartilage layer correspond to a part stained by a compound. Some of the circular regions (blue in a color photo) correspond to nuclear stain parts by Hoechst, which were also observed in the calcified layer.

Kε1-NBD: compound 26
Kε3-NBD: compound 27
Kε4-NBD: compound 28
Kε5-NBD: compound 29

[Immersion of a Swine Knee Joint Cartilage in a Solution of a Radiographic Contrast Agent and Evaluation by X-Ray CT Imaging]

Apiece of swine knee joint cartilage purchased from a shop of the Agricultural Cooperative Association was sliced into about 1.0×0.5×0.2 cm pieces with a razor. These cartilage slices were immersed in a 200 mM solution of compound D (compound 48: Kε5-TIB) in phosphate buffer or phosphate buffer alone for 30 min. Thirty minutes later, every cartilage slice was rinsed with phosphate buffer and washed, and the excess water was wiped with Kimwipes. Every cartilage slice sample was subjected to imaging and image reconstruction in a 10.7 μm isotropic voxel using a micro-CT analysis system (SkyScan 1174, SkyScan, Aartselaar, Belgium). The electronic data thus obtained were further scrutinized using a volumetric reconstruction software (NRecon, CTAn, CTvol•CTVox, SkyScan) to give a CT image.

FIG. 3 is an X-ray CT image obtained. In FIG. 3, "Kε5-TIB" is a sample immersed in an aqueous solution of compound 48, and "PBS" is a sample immersed in phosphate buffer alone. For each sample, two images were taken from different directions. In the images, the net-like region in the cartilage image is a calcified layer, over which there is a cartilage layer. A cartilage layer is not observed for the sample with immersion in PBS alone, while a cartilage layer is observed as a white part for the sample immersed in the compound D solution. Since shading are also clearly observed, the photos can give information not only about a thickness of the cartilage layer but also about a concentration of chondroitin sulfate contained therein and so on.

The invention claimed is:

1. A cartilage tissue marker made of a lysine oligomer consisting of 3 to 5 lysines represented by formula (I) or a pharmaceutically acceptable salt thereof

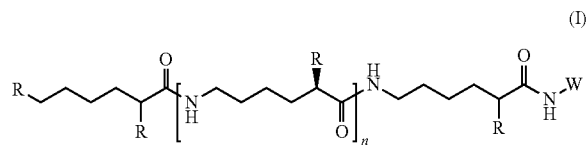

wherein n is an integer, R is NH$_2$; and of 1 to 3;

W is selected from the group consisting of an iodine-containing benzoic acid derivative, a benzofurazan dye, a rhodamine dye, a fluorescein dye, a cyanine dye, an Atto dye, a BODIPY dye, Cascade Blue, Oregon Green dye, Rhodol Green, Texas Red, and fluorescent dyes sold under the trademarks of ALEXA FLUOR®, VIVOTAG®, and CAL FLUOR®.

2. The cartilage tissue marker according to claim 1, wherein the iodine-containing benzoic acid derivative is a triiodobenzene derivative.

3. The cartilage tissue marker according to claim 1, wherein W is a benzofurazan dye.

4. The cartilage tissue marker according to claim 1, wherein the lysine oligomer consisits of 3 or 4 lysines and n is 1 or 2.

5. The cartilage tissue marker according to claim 4, wherein the iodine-containing benzoic acid derivative is a triiodobenzene derivative.

6. The cartilage tissue marker according to claim 4, wherein W is a benzofurazan dye.

\* \* \* \* \*

UNITED STATES PATENT AND TRADEMARK OFFICE
CERTIFICATE OF CORRECTION

| | | |
|---|---|---|
| PATENT NO. | : 9,724,434 B2 | Page 1 of 1 |
| APPLICATION NO. | : 14/383976 | |
| DATED | : August 8, 2017 | |
| INVENTOR(S) | : Toshitaka Oohashi et al. | |

It is certified that error appears in the above-identified patent and that said Letters Patent is hereby corrected as shown below:

In the Claims

In Column 41, Line 15 replace:
--n is an integer, R is $NH_2$; and of 1 to 3--
With:
"n is an integer of 1 to 3, R is $NH_2$; and"

Signed and Sealed this
Fifth Day of December, 2017

Joseph Matal
*Performing the Functions and Duties of the*
*Under Secretary of Commerce for Intellectual Property and*
*Director of the United States Patent and Trademark Office*